United States Patent [19]

Coughlin

[11] Patent Number: 5,256,766
[45] Date of Patent: Oct. 26, 1993

[54] RECOMBINANT THROMBIN RECEPTOR AND RELATED PHARMACEUTICALS

[75] Inventor: Shaun R. Coughlin, San Francisco, Calif.

[73] Assignee: The Regents of the University of California, Oakland, Calif.

[21] Appl. No.: 657,769

[22] Filed: Feb. 19, 1991

[51] Int. Cl.$^5$ ............................................. A61K 37/02
[52] U.S. Cl. ..................... 530/327; 530/328; 530/329; 530/330
[58] Field of Search ............... 530/327, 328, 329, 330; 435/69.1

[56]       References Cited
        U.S. PATENT DOCUMENTS 4,859,609  8/1989  Dull et al. ........................ 436/501

OTHER PUBLICATIONS

Biochem. & Biophys Res. Comm. 184:790–796, Apr. 30, 1992, Hui et al. Minimal Sequences Requirement of Thrombin Receptor Agonist Peptides.
Masu et al., *Nature* (1987) 329836–838.
Ruda et al., *Biochemical Pharmacology* (1990) 39(2):373–381.
Ruda et al., *Annals New York Academy of Sciences* (1986) 485:439–442.
Walz et al., *Annals New York Academy of Sciences* (1986) 485:323–334.
Bar-Shavit et al., *Journal of Cell Biology* (1991) 112(2):335–344.
Gronke et al., *J. Biol. Chem.* (1987) 262:3030–3036.
Okamura et al., *J. Biol. Chem.* (1978) 253:3455–.
Berndt et al., "Platelets in Biology and Pathology" (1981) Elsevier/North Holland Biomedical Press, pp. 43–74.
Martin et al., *Biochem.* (1975) 14:1308–1314.
Tollefsen et al., *J. Biol. Chem.* (1974) 249:2646–2651.
Phillips, *Thrombin Diath. Haemorrh.* (1974) 32:207–215.
Workman et al., *J. Biol. Chem.* (1977) 252:7118–7123.
Greco et al., *Blood* (1990) 75:1983–1990.
Bode et al., *EMBO J.* (1989) 8:3467–3475.
Van Obberghen-Shilling et al., *FEBS Letters* (1990) 262:330–334.
Pipili-Synetos et al.,*Biochem. Biophys. Res. Comm. (1990) 171:913–919.

*Primary Examiner*—Robert J. Hill, Jr.
*Assistant Examiner*—John D. Ulm
*Attorney, Agent, or Firm*—Morrison & Foerster

[57]            ABSTRACT

The DNA encoding the cell surface receptor for thrombin has been cloned and sequenced. The availability of this DNA permits the recombinant production of thrombin receptor which can be produced at cell surfaces and is useful in assay systems both for the detection of thrombin and for the evaluation of candidate thrombin agonists and antagonists. Further, the elucidation of the structure of the thrombin receptor permits the design of agonist and antagonist compounds which are useful diagnostically and therapeutically. The availability of the thrombin receptor also permits production of antibodies specifically immunoreactive with the receptor per se or with specific regions thereof.

16 Claims, 10 Drawing Sheets

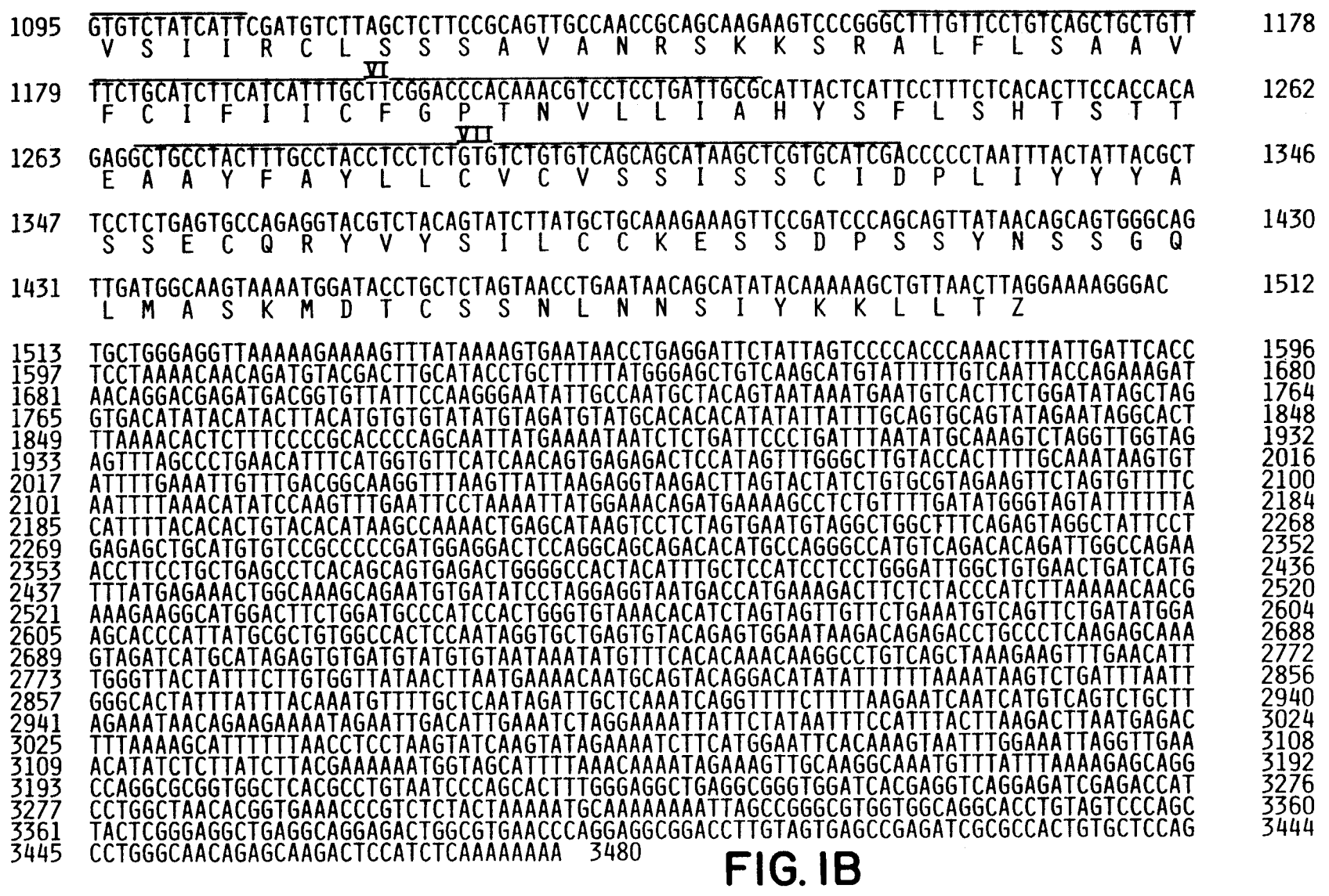

SEQUENCE LISTING ( 1 ) GENERAL INFORMATION:

( i i i ) NUMBER OF SEQUENCES: 69

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Leu Asp Pro Arg Pro
1                 5

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:2:

Arg Pro Glu Ser Lys Ala Thr Asn Ala Thr Leu Asp Pro Arg
1               5                   10

( 2 ) INFORMATION FOR SEQ ID NO:3:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

Tyr Glu Pro Phe Trp Glu Asp Glu Glu
1               5

( 2 ) INFORMATION FOR SEQ ID NO:4:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

Ser Phe Leu Leu Arg Asn Pro Asn Asp Lys Tyr Glu Pro Phe
1               5                   10

( 2 ) INFORMATION FOR SEQ ID NO:5:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Ser  Phe  Leu  Leu  Arg  Asn  Pro  Asn  Asp  Lys  Tyr  Glu  Pro
1                   5                        10
```

(2) INFORMATION FOR SEQ ID NO:6:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:6:

```
Ser  Phe  Leu  Leu  Arg  Asn  Pro  Asn  Asp  Lys  Tyr  Glu
1                   5                        10
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO:7:

```
Ser  Phe  Leu  Leu  Arg  Asn  Pro  Asn  Asp  Lys  Tyr
1                   5                        10
```

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:8:

```
Ser  Phe  Leu  Leu  Arg  Asn  Pro  Asn  Asp  Lys
1                   5                        10
```

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:9:

```
Ser  Phe  Leu  Leu  Arg  Asn  Pro  Asn  Asp
1                   5
```

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:10:

```
Ser  Phe  Leu  Leu  Arg  Asn  Pro  Asn
1                   5
```

(2) INFORMATION FOR SEQ ID NO:11:

(i) SEQUENCE CHARACTERISTICS:
        (A) LENGTH: 7 amino acids
        (B) TYPE: amino acid
        (C) STRANDEDNESS: single
        (D) TOPOLOGY: linear ( x i ) SEQUENCE DESCRIPTION: SEQ ID NO:11:

Ser Phe Leu Leu Arg Asn Pro
1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

Ser Phe Leu Leu Arg Asn
1               5

( 2 ) INFORMATION FOR SEQ ID NO:13:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:13:

Ser Phe Leu Leu Arg
1               5

( 2 ) INFORMATION FOR SEQ ID NO:14:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:14:

Ser Phe Leu Leu
1

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:15:

Trp Glu Asp Glu Glu
1               5

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:16:

Trp Gln Asp Gln Gln
1               5

( 2 ) INFORMATION FOR SEQ ID NO:17:

( i ) SEQUENCE CHARACTERISTICS:
        ( A ) LENGTH: 5 amino acids
        ( B ) TYPE: amino acid ( C ) STRANDEDNESS: single
( D ) TOPOLOGY: linear ( x i ) SEQUENCE DESCRIPTION: SEQ ID NO:17:

Trp Glu Asp Glu Gln
1               5

( 2 ) INFORMATION FOR SEQ ID NO:18:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:18:

Trp Gln Asp Glu Gln
1               5

( 2 ) INFORMATION FOR SEQ ID NO:19:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:19:

Trp Gln Asp Glu Glu
1               5

( 2 ) INFORMATION FOR SEQ ID NO:20:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:20:

Trp Glu Asp Gln Glu
1               5

( 2 ) INFORMATION FOR SEQ ID NO:21:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:21:

Trp Glu Asp Gln Gln
1               5

( 2 ) INFORMATION FOR SEQ ID NO:22:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( x i ) SEQUENCE DESCRIPTION: SEQ ID NO:22:

Trp Gln Asp Gln Glu
1               5

( 2 ) INFORMATION FOR SEQ ID NO:23:

( i ) SEQUENCE CHARACTERISTICS:

(A) LENGTH: 5 amino acids
(B) TYPE: amino acid
(C) STRANDEDNESS: single
(D) TOPOLOGY: linear (xi) SEQUENCE DESCRIPTION: SEQ ID NO:23:

Leu Asp Pro Arg Pro
1               5

(2) INFORMATION FOR SEQ ID NO:24:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:24:

Leu Glu Pro Arg Pro
1               5

(2) INFORMATION FOR SEQ ID NO:25:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:25:

Ile Asp Pro Arg Pro
1               5

(2) INFORMATION FOR SEQ ID NO:26:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:26:

Ile Glu Pro Arg Pro
1               5

(2) INFORMATION FOR SEQ ID NO:27:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:27:

Val Asp Pro Arg Pro
1               5

(2) INFORMATION FOR SEQ ID NO:28:

(i) SEQUENCE CHARACTERISTICS:
(A) LENGTH: 5 amino acids
(B) TYPE: amino acid
(C) STRANDEDNESS: single
(D) TOPOLOGY: linear (xi) SEQUENCE DESCRIPTION: SEQ ID NO:28:

Val Glu Pro Arg Pro
1               5

(2) INFORMATION FOR SEQ ID NO:29:

( i ) SEQUENCE CHARACTERISTICS:
(A) LENGTH: 27 amino acids
(B) TYPE: amino acid
(C) STRANDEDNESS: single
(D) TOPOLOGY: linear ( x i ) SEQUENCE DESCRIPTION: SEQ ID NO:29:

```
Leu Asp Pro Arg Pro Phe Leu Leu Arg Asn Pro Asn Asp Lys Tyr Glu
1               5                   10                  15
Pro Phe Trp Glu Asp Glu Glu Lys Asn Glu Ser
            20                  25
```

( 2 ) INFORMATION FOR SEQ ID NO:30:

( i ) SEQUENCE CHARACTERISTICS:
(A) LENGTH: 26 amino acids
(B) TYPE: amino acid
(C) STRANDEDNESS: single
(D) TOPOLOGY: linear ( x i ) SEQUENCE DESCRIPTION: SEQ ID NO:30:

```
Leu Asp Pro Arg Pro Phe Leu Leu Arg Asn Pro Asn Asp Lys Tyr Glu
1               5                   10                  15
Pro Phe Trp Glu Asp Glu Glu Lys Asn Glu
            20                  25
```

( 2 ) INFORMATION FOR SEQ ID NO:31:

( i ) SEQUENCE CHARACTERISTICS:
(A) LENGTH: 25 amino acids
(B) TYPE: amino acid
(C) STRANDEDNESS: single
(D) TOPOLOGY: linear ( x i ) SEQUENCE DESCRIPTION: SEQ ID NO:31:

```
Leu Asp Pro Arg Pro Phe Leu Leu Arg Asn Pro Asn Asp Lys Tyr Glu
1               5                   10                  15
Pro Phe Trp Glu Asp Glu Glu Lys Asn
            20                  25
```

( 2 ) INFORMATION FOR SEQ ID NO:32:

( i ) SEQUENCE CHARACTERISTICS:
(A) LENGTH: 24 amino acids
(B) TYPE: amino acid
(C) STRANDEDNESS: single
(D) TOPOLOGY: linear ( x i ) SEQUENCE DESCRIPTION: SEQ ID NO:32:

```
Leu Asp Pro Arg Pro Phe Leu Leu Arg Asn Pro Asn Asp Lys Tyr Glu
1               5                   10                  15
Pro Phe Trp Glu Asp Glu Glu Lys
            20
```

( 2 ) INFORMATION FOR SEQ ID NO:33:

( i ) SEQUENCE CHARACTERISTICS:
(A) LENGTH: 23 amino acids
(B) TYPE: amino acid
(C) STRANDEDNESS: single
(D) TOPOLOGY: linear ( x i ) SEQUENCE DESCRIPTION: SEQ ID NO:33:

```
Leu Asp Pro Arg Pro Phe Leu Leu Arg Asn Pro Asn Asp Lys Tyr Glu
1               5                   10                  15
Pro Phe Trp Glu Asp Glu Glu
            20
```

( 2 ) INFORMATION FOR SEQ ID NO:34:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( x i ) SEQUENCE DESCRIPTION: SEQ ID NO:34:

```
Leu Asp Pro Arg Pro Phe Leu Leu Arg Asn Pro Asn Asp Lys Tyr Glu
1               5                   10                  15
Pro Phe Trp Glu Asp Glu
            20
```

( 2 ) INFORMATION FOR SEQ ID NO:35:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( x i ) SEQUENCE DESCRIPTION: SEQ ID NO:35:

```
Leu Asp Pro Arg Pro Phe Leu Leu Arg Asn Pro Asn Asp Lys Tyr Glu
1               5                   10                  15
Pro Phe Trp Glu Asp
            20
```

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:36:

```
Trp Lys Lys Lys Lys
1               5
```

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:37:

```
Lys Lys Lys Lys Trp
1               5
```

( 2 ) INFORMATION FOR SEQ ID NO:38:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:38:

```
Gln Lys Gln Gln Trp
1               5
```

( 2 ) INFORMATION FOR SEQ ID NO:39:

( i ) SEQUENCE CHARACTERISTICS:
        ( A ) LENGTH: 5 amino acids ( B ) TYPE: amino acid
( C ) STRANDEDNESS: single
( D ) TOPOLOGY: linear ( x i ) SEQUENCE DESCRIPTION: SEQ ID NO:39:

Trp Gln Lys Gln Gln
1               5

( 2 ) INFORMATION FOR SEQ ID NO:40:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( x i ) SEQUENCE DESCRIPTION: SEQ ID NO:40:

Leu Asp Pro Arg Ser Phe Leu Leu
1               5

( 2 ) INFORMATION FOR SEQ ID NO:41:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( x i ) SEQUENCE DESCRIPTION: SEQ ID NO:41:

Tyr Tyr Phe Ser Gly Ser Asp Trp Gln Phe Gly Ser Glu Leu Cys Arg
1               5                   10                  15

( 2 ) INFORMATION FOR SEQ ID NO:42:

( i ) SEQUENCE CHARACTERISTICS:
( A ) LENGTH: 26 amino acids
( B ) TYPE: amino acid
( C ) STRANDEDNESS: single
( D ) TOPOLOGY: linear ( x i ) SEQUENCE DESCRIPTION: SEQ ID NO:42:

Lys Glu Gln Thr Ile Gln Val Pro Gly Leu Asn Ile Thr Thr Cys His
1               5                   10                  15

Asp Val Leu Asn Glu Thr Leu Leu Glu Gly
            20                  25

( 2 ) INFORMATION FOR SEQ ID NO:43:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( x i ) SEQUENCE DESCRIPTION: SEQ ID NO:43:

His Tyr Ser Phe Leu Ser His Thr Ser Thr Thr
1               5                   10

( 2 ) INFORMATION FOR SEQ ID NO:44:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( x i ) SEQUENCE DESCRIPTION: SEQ ID NO:44:

Xaa Phe Leu Leu Arg Asn Pro Asn Asp Lys Tyr Glu Pro Phe
1               5                   10

( 2 ) INFORMATION FOR SEQ ID NO:45:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( x i ) SEQUENCE DESCRIPTION: SEQ ID NO:45:

```
Xaa Phe Leu Leu Arg Asn Pro Asn Asp Lys Tyr Glu Pro
 1               5                  10
```

( 2 ) INFORMATION FOR SEQ ID NO:46:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( x i ) SEQUENCE DESCRIPTION: SEQ ID NO:46:

```
Xaa Phe Leu Leu Arg Asn Pro Asn Asp Lys Tyr Glu
 1               5                  10
```

( 2 ) INFORMATION FOR SEQ ID NO:47:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( x i ) SEQUENCE DESCRIPTION: SEQ ID NO:47:

```
Xaa Phe Leu Leu Arg Asn Pro Asn Asp Lys Tyr
 1               5                  10
```

( 2 ) INFORMATION FOR SEQ ID NO:48:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( x i ) SEQUENCE DESCRIPTION: SEQ ID NO:48:

```
Xaa Phe Leu Leu Arg Asn Pro Asn Asp Lys
 1               5                  10
```

( 2 ) INFORMATION FOR SEQ ID NO:49:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( x i ) SEQUENCE DESCRIPTION: SEQ ID NO:49:

```
Xaa Phe Leu Leu Arg Asn Pro Asn Asp
 1               5
```

( 2 ) INFORMATION FOR SEQ ID NO:50:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( x i ) SEQUENCE DESCRIPTION: SEQ ID NO:50:

```
Xaa Phe Leu Leu Arg Asn Pro Asn
```

(2) INFORMATION FOR SEQ ID NO:51:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:51:

Xaa  Phe  Leu  Leu  Arg  Asn  Pro
  1                     5

(2) INFORMATION FOR SEQ ID NO:52:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:52:

Xaa  Phe  Leu  Leu  Arg  Asn
  1                   5

(2) INFORMATION FOR SEQ ID NO:53:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:53:

Xaa  Phe  Leu  Leu  Arg
  1                5

(2) INFORMATION FOR SEQ ID NO:54:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:54:

Xaa  Phe  Leu  Leu
  1

(2) INFORMATION FOR SEQ ID NO:55:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:55:

Arg  Pro  Glu  Ser  Lys
  1                 5

(2) INFORMATION FOR SEQ ID NO:56:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO:56:

```
     Phe  Ser  Leu  Leu  Arg  Asn  Pro  Asn  Asp  Lys  Tyr  Glu  Pro  Phe
     1              5                        10
```

( 2 ) INFORMATION FOR SEQ ID NO:57:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:57:

```
     Leu  Leu  Arg  Asn  Pro  Asn  Asp  Lys  Tyr  Glu  Pro  Phe
     1              5                        10
```

( 2 ) INFORMATION FOR SEQ ID NO:58:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:58:

```
     Phe  Ser  Leu  Leu
     1
```

( 2 ) INFORMATION FOR SEQ ID NO:59:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:59:

```
     Ala  Pro  Met  Ser  Phe
     1              5
```

( 2 ) INFORMATION FOR SEQ ID NO:60:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( x i ) SEQUENCE DESCRIPTION: SEQ ID NO:60:

```
     Arg  Pro  Glu  Ser  Lys  Ala  Thr  Asn  Ala  Thr  Leu  Asp  Pro  Arg  Ser  Phe
     1              5                        10                            15
     Leu  Leu  Arg  Asn  Pro  Asn  Asp  Lys  Tyr  Glu  Pro  Phe  Trp  Glu  Asp  Glu
                  20                        25                            30
     Glu  Lys  Asn  Glu  Ser
                  35
```

( 2 ) INFORMATION FOR SEQ ID NO:61:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( x i ) SEQUENCE DESCRIPTION: SEQ ID NO:61:

```
     Arg  Pro  Glu  Ser  Lys  Ala  Thr  Asn  Ala  Thr  Leu  Asp  Pro  Arg
     1              5                        10
```

( 2 ) INFORMATION FOR SEQ ID NO:62:

( i ) SEQUENCE CHARACTERISTICS:
 ( A ) LENGTH: 5 amino acids
 ( B ) TYPE: amino acid
 ( C ) STRANDEDNESS: single
 ( D ) TOPOLOGY: linear ( x i ) SEQUENCE DESCRIPTION: SEQ ID NO:62:

Leu Asp Pro Arg Pro
1               5

( 2 ) INFORMATION FOR SEQ ID NO:63:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:63:

Leu Glu Pro Arg Pro
1               5

( 2 ) INFORMATION FOR SEQ ID NO:64:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:64:

Ile Asp Pro Arg Pro
1               5

( 2 ) INFORMATION FOR SEQ ID NO:65:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:65:

Ile Glu Pro Arg Pro
1               5

( 2 ) INFORMATION FOR SEQ ID NO:66:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:66:

Val Asp Pro Arg Pro
1               5

( 2 ) INFORMATION FOR SEQ ID NO:67:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( x i ) SEQUENCE DESCRIPTION: SEQ ID NO:67:

Val Glu Pro Arg Pro
1               5

-continued ( 2 ) INFORMATION FOR SEQ ID NO:68:

( i ) SEQUENCE CHARACTERISTICS:
        ( A ) LENGTH: 3480 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 225..1503

( x i ) SEQUENCE DESCRIPTION: SEQ ID NO:68:

```
GCGCCCGCGC GACCGCGCGC CCCAGTCCCG CCCCGCCCCG CTAACCGCCC CAGACACAGC        60

GCTCGCCGAG GGTCGCTTGG ACCCTGATCT TACCCGTGGG CACCCTGCGC TCTGCCTGCC       120

GCGAAGACCG GCTCCCCGAC CCGCAGAAGT CAGGAGAGAG GGTGAAGCGG AGCAGCCCGA       180

GGCGGGGCAG CCTCCCGGAG CAGCGCCGCG CAGAGCCCGG GACA ATG GGG CCG CGG       236
                                                  Met Gly Pro Arg
                                                    1

CGG CTG CTG CTG GTG GCC GCC TGC TTC AGT CTG TGC GGC CCG CTG TTG       284
Arg Leu Leu Leu Val Ala Ala Cys Phe Ser Leu Cys Gly Pro Leu Leu
  5              10                 15                  20

TCT GCC CGC ACC CGG GCC CGC AGG CCA GAA TCA AAA GCA ACA AAT GCC       332
Ser Ala Arg Thr Arg Ala Arg Arg Pro Glu Ser Lys Ala Thr Asn Ala
             25                  30                  35

ACC TTA GAT CCC CGG TCA TTT CTT CTC AGG AAC CCC AAT GAT AAA TAT       380
Thr Leu Asp Pro Arg Ser Phe Leu Leu Arg Asn Pro Asn Asp Lys Tyr
         40                  45                  50

GAA CCA TTT TGG GAG GAT GAG GAG AAA AAT GAA AGT GGG TTA ACT GAA       428
Glu Pro Phe Trp Glu Asp Glu Glu Lys Asn Glu Ser Gly Leu Thr Glu
             55                  60                  65

TAC AGA TTA GTC TCC ATC AAT AAA AGC AGT CCT CTT CAA AAA CAA CTT       476
Tyr Arg Leu Val Ser Ile Asn Lys Ser Ser Pro Leu Gln Lys Gln Leu
     70                  75                  80

CCT GCA TTC ATC TCA GAA GAT GCC TCC GGA TAT TTG ACC AGC TCC TGG       524
Pro Ala Phe Ile Ser Glu Asp Ala Ser Gly Tyr Leu Thr Ser Ser Trp
 85                  90                  95                 100

CTG ACA CTC TTT GTC CCA TCT GTG TAC ACC GGA GTG TTT GTA GTC AGC       572
Leu Thr Leu Phe Val Pro Ser Val Tyr Thr Gly Val Phe Val Val Ser
                 105                 110                 115

CTC CCA CTA AAC ATC ATG GCC ATC GTT GTG TTC ATC CTG AAA ATG AAG       620
Leu Pro Leu Asn Ile Met Ala Ile Val Val Phe Ile Leu Lys Met Lys
             120                 125                 130

GTC AAG AAG CCG GCG GTG GTG TAC ATG CTG CAC CTG GCC ACG GCA GAT       668
Val Lys Lys Pro Ala Val Val Tyr Met Leu His Leu Ala Thr Ala Asp
         135                 140                 145

GTG CTG TTT GTG TCT GTG CTC CCC TTT AAG ATC AGC TAT TAC TTT TCC       716
Val Leu Phe Val Ser Val Leu Pro Phe Lys Ile Ser Tyr Tyr Phe Ser
 150                 155                 160

GGC AGT GAT TGG CAG TTT GGG TCT GAA TTG TGT CGC TTC GTC ACT GCA       764
Gly Ser Asp Trp Gln Phe Gly Ser Glu Leu Cys Arg Phe Val Thr Ala
165                 170                 175                 180

GCA TTT TAC TGT AAC ATG TAC GCC TCT ATC TTG CTC ATG ACA GTC ATA       812
Ala Phe Tyr Cys Asn Met Tyr Ala Ser Ile Leu Leu Met Thr Val Ile
                 185                 190                 195

AGC ATT GAC CGG TTT CTG GCT GTG GTG TAT CCC ATG CAG TCC CTC TCC       860
Ser Ile Asp Arg Phe Leu Ala Val Val Tyr Pro Met Gln Ser Leu Ser
             200                 205                 210

TGG CGT ACT CTG GGA AGG GCT TCC TTC ACT TGT CTG GCC ATC TGG GCT       908
Trp Arg Thr Leu Gly Arg Ala Ser Phe Thr Cys Leu Ala Ile Trp Ala
```

|  |  |  |  |  |  |  |  |  |  |  |  |  |  |  |  |  |
|---|---|---|---|---|---|---|---|---|---|---|---|---|---|---|---|---|
|  |  | 215 |  |  |  |  | 220 |  |  |  |  |  | 225 |  |  |  |
| TTG | GCC | ATC | GCA | GGG | GTA | GTG | CCT | CTC | GTC | CTC | AAG | GAG | CAA | ACC | ATC | 956 |
| Leu | Ala | Ile | Ala | Gly | Val | Val | Pro | Leu | Val | Leu | Lys | Glu | Gln | Thr | Ile |  |
|  |  | 230 |  |  |  |  | 235 |  |  |  |  | 240 |  |  |  |  |
| CAG | GTG | CCC | GGG | CTC | AAC | ATC | ACT | ACC | TGT | CAT | GAT | GTG | CTC | AAT | GAA | 1004 |
| Gln | Val | Pro | Gly | Leu | Asn | Ile | Thr | Thr | Cys | His | Asp | Val | Leu | Asn | Glu |  |
| 245 |  |  |  |  | 250 |  |  |  |  | 255 |  |  |  |  | 260 |  |
| ACC | CTG | CTC | GAA | GGC | TAC | TAT | GCC | TAC | TAC | TTC | TCA | GCC | TTC | TCT | GCT | 1052 |
| Thr | Leu | Leu | Glu | Gly | Tyr | Tyr | Ala | Tyr | Tyr | Phe | Ser | Ala | Phe | Ser | Ala |  |
|  |  |  |  |  | 265 |  |  |  | 270 |  |  |  |  | 275 |  |  |
| GTC | TTC | TTT | TTT | GTG | CCG | CTG | ATC | ATT | TCC | ACG | GTC | TGT | TAT | GTG | TCT | 1100 |
| Val | Phe | Phe | Phe | Val | Pro | Leu | Ile | Ile | Ser | Thr | Val | Cys | Tyr | Val | Ser |  |
|  |  |  | 280 |  |  |  |  | 285 |  |  |  |  | 290 |  |  |  |
| ATC | ATT | CGA | TGT | CTT | AGC | TCT | TCC | GCA | GTT | GCC | AAC | CGC | AGC | AAG | AAG | 1148 |
| Ile | Ile | Arg | Cys | Leu | Ser | Ser | Ser | Ala | Val | Ala | Asn | Arg | Ser | Lys | Lys |  |
|  |  | 295 |  |  |  |  | 300 |  |  |  |  | 305 |  |  |  |  |
| TCC | CGG | GCT | TTG | TTC | CTG | TCA | GCT | GCT | GTT | TTC | TGC | ATC | TTC | ATC | ATT | 1196 |
| Ser | Arg | Ala | Leu | Phe | Leu | Ser | Ala | Ala | Val | Phe | Cys | Ile | Phe | Ile | Ile |  |
|  | 310 |  |  |  |  | 315 |  |  |  |  | 320 |  |  |  |  |  |
| TGC | TTC | GGA | CCC | ACA | AAC | GTC | CTC | CTG | ATT | GCG | CAT | TAC | TCA | TTC | CTT | 1244 |
| Cys | Phe | Gly | Pro | Thr | Asn | Val | Leu | Leu | Ile | Ala | His | Tyr | Ser | Phe | Leu |  |
| 325 |  |  |  |  | 330 |  |  |  |  | 335 |  |  |  |  | 340 |  |
| TCT | CAC | ACT | TCC | ACC | ACA | GAG | GCT | GCC | TAC | TTT | GCC | TAC | CTC | CTC | TGT | 1292 |
| Ser | His | Thr | Ser | Thr | Thr | Glu | Ala | Ala | Tyr | Phe | Ala | Tyr | Leu | Leu | Cys |  |
|  |  |  |  | 345 |  |  |  |  | 350 |  |  |  |  | 355 |  |  |
| GTC | TGT | GTC | AGC | AGC | ATA | AGC | TCG | TGC | ATC | GAC | CCC | CTA | ATT | TAC | TAT | 1340 |
| Val | Cys | Val | Ser | Ser | Ile | Ser | Ser | Cys | Ile | Asp | Pro | Leu | Ile | Tyr | Tyr |  |
|  |  |  | 360 |  |  |  |  | 365 |  |  |  |  | 370 |  |  |  |
| TAC | GCT | TCC | TCT | GAG | TGC | CAG | AGG | TAC | GTC | TAC | AGT | ATC | TTA | TGC | TGC | 1388 |
| Tyr | Ala | Ser | Ser | Glu | Cys | Gln | Arg | Tyr | Val | Tyr | Ser | Ile | Leu | Cys | Cys |  |
|  |  | 375 |  |  |  |  | 380 |  |  |  |  | 385 |  |  |  |  |
| AAA | GAA | AGT | TCC | GAT | CCC | AGC | AGT | TAT | AAC | AGC | AGT | GGG | CAG | TTG | ATG | 1436 |
| Lys | Glu | Ser | Ser | Asp | Pro | Ser | Ser | Tyr | Asn | Ser | Ser | Gly | Gln | Leu | Met |  |
|  | 390 |  |  |  |  | 395 |  |  |  |  | 400 |  |  |  |  |  |
| GCA | AGT | AAA | ATG | GAT | ACC | TGC | TCT | AGT | AAC | CTG | AAT | AAC | AGC | ATA | TAC | 1484 |
| Ala | Ser | Lys | Met | Asp | Thr | Cys | Ser | Ser | Asn | Leu | Asn | Asn | Ser | Ile | Tyr |  |
| 405 |  |  |  |  | 410 |  |  |  |  | 415 |  |  |  |  | 420 |  |
| AAA | AAG | CTG | TTA | ACT | TAG | G | AAAAGGGACT | GCTGGGAGGT | TAAAAAGAAA |  |  |  |  |  |  | 1533 |
| Lys | Lys | Leu | Leu | Thr |  |  |  |  |  |  |  |  |  |  |  |  |
|  |  |  |  | 425 |  |  |  |  |  |  |  |  |  |  |  |  |

| | | |
|---|---|---|
| AGTTTATAAA AGTGAATAAC CTGAGGATTC TATTAGTCCC CACCCAAACT TTATTGATTC | 1593 |
| ACCTCCTAAA ACAACAGATG TACGACTTGC ATACCTGCTT TTTATGGGAG CTGTCAAGCA | 1653 |
| TGTATTTTTG TCAATTACCA GAAAGATAAC AGGACGAGAT GACGGTGTTA TTCCAAGGGA | 1713 |
| ATATTGCCAA TGCTACAGTA ATAAATGAAT GTCACTTCTG GATATAGCTA GGTGACATAT | 1773 |
| ACATACTTAC ATGTGTGTAT ATGTAGATGT ATGCACACAC ATATATTATT TGCAGTGCAG | 1833 |
| TATAGAATAG GCACTTTAAA ACACTCTTTC CCCGCACCCC AGCAATTATG AAAATAATCT | 1893 |
| CTGATTCCCT GATTTAATAT GCAAAGTCTA GGTTGGTAGA GTTTAGCCCT GAACATTTCA | 1953 |
| TGGTGTTCAT CAACAGTGAG AGACTCCATA GTTTGGGCTT GTACCACTTT TGCAAATAAG | 2013 |
| TGTATTTTGA AATTGTTTGA CGGCAAGGTT TAAGTTATTA AGAGGTAAGA CTTAGTACTA | 2073 |
| TCTGTGCGTA GAAGTTCTAG TGTTTTCAAT TTTAAACATA TCCAAGTTTG AATTCCTAAA | 2133 |
| ATTATGGAAA CAGATGAAAA GCCTCTGTTT TGATATGGGT AGTATTTTTT ACATTTTACA | 2193 |
| CACTGTACAC ATAAGCCAAA ACTGAGCATA AGTCCTCTAG TGAATGTAGG CTGGCTTTCA | 2253 |
| GAGTAGGCTA TTCCTGAGAG CTGCATGTGT CCGCCCCCGA TGGAGGACTC CAGGCAGCAG | 2313 |
| ACACATGCCA GGGCCATGTC AGACACAGAT TGGCCAGAAA CCTTCCTGCT GAGCCTCACA | 2373 |

-continued

| | | | | |
|---|---|---|---|---|
| GCAGTGAGAC | TGGGGCCACT | ACATTTGCTC | CATCCTCCTG | GGATTGGCTG | TGAACTGATC | 2433 |
| ATGTTTATGA | GAAACTGGCA | AAGCAGAATG | TGATATCCTA | GGAGGTAATG | ACCATGAAAG | 2493 |
| ACTTCTCTAC | CCATCTTAAA | AACAACGAAA | GAAGGCATGG | ACTTCTGGAT | GCCCATCCAC | 2553 |
| TGGGTGTAAA | CACATCTAGT | AGTTGTTCTG | AAATGTCAGT | TCTGATATGG | AAGCACCCAT | 2613 |
| TATGCGCTGT | GGCCACTCCA | ATAGGTGCTG | AGTGTACAGA | GTGGAATAAG | ACAGAGACCT | 2673 |
| GCCCTCAAGA | GCAAAGTAGA | TCATGCATAG | AGTGTGATGT | ATGTGTAATA | AATATGTTTC | 2733 |
| ACACAAACAA | GGCCTGTCAG | CTAAAGAAGT | TTGAACATTT | GGGTTACTAT | TTCTTGTGGT | 2793 |
| TATAACTTAA | TGAAAACAAT | GCAGTACAGG | ACATATATTT | TTTAAAATAA | GTCTGATTTA | 2853 |
| ATTGGGCACT | ATTTATTTAC | AAATGTTTTG | CTAATAGAT | TGCTCAAATC | AGGTTTTCTT | 2913 |
| TTAAGAATCA | ATCATGTCAG | TCTGCTTAGA | AATAACAGAA | GAAATAGAA | TTGACATTGA | 2973 |
| AATCTAGGAA | AATTATTCTA | TAATTTCCAT | TTACTTAAGA | CTTAATGAGA | CTTTAAAAGC | 3033 |
| ATTTTTTAAC | CTCCTAAGTA | TCAAGTATAG | AAAATCTTCA | TGGAATTCAC | AAAGTAATTT | 3093 |
| GGAAATTAGG | TTGAAACATA | TCTCTTATCT | TACGAAAAAA | TGGTAGCATT | TTAAACAAAA | 3153 |
| TAGAAAGTTG | CAAGGCAAAT | GTTTATTTAA | AAGAGCAGGC | CAGGCGCGGT | GGCTCACGCC | 3213 |
| TGTAATCCCA | GCACTTTGGG | AGGCTGAGGC | GGGTGGATCA | CGAGGTCAGG | AGATCGAGAC | 3273 |
| CATCCTGGCT | AACACGGTGA | AACCCGTCTC | TACTAAAAAT | GCAAAAAAA | TTAGCCGGGC | 3333 |
| GTGGTGGCAG | GCACCTGTAG | TCCCAGCTAC | TCGGGAGGCT | GAGGCAGGAG | ACTGGCGTGA | 3393 |
| ACCCAGGAGG | CGGACCTTGT | AGTGAGCCGA | GATCGCGCCA | CTGTGCTCCA | GCCTGGGCAA | 3453 |
| CAGAGCAAGA | CTCCATCTCA | AAAAAA | | | | 3480 |

( 2 ) INFORMATION FOR SEQ ID NO:69:

( i ) SEQUENCE CHARACTERISTICS:
( A ) LENGTH: 425 amino acids
( B ) TYPE: amino acid
( D ) TOPOLOGY: linear ( i i ) MOLECULE TYPE: protein ( x i ) SEQUENCE DESCRIPTION: SEQ ID NO:69:

```
Met Gly Pro Arg Arg Leu Leu Leu Val Ala Ala Cys Phe Ser Leu Cys
 1               5                  10                  15

Gly Pro Leu Leu Ser Ala Arg Thr Ala Arg Arg Pro Glu Ser Lys
            20                  25                  30

Ala Thr Asn Ala Thr Leu Asp Pro Arg Ser Phe Leu Leu Arg Asn Pro
        35                  40                  45

Asn Asp Lys Tyr Glu Pro Phe Trp Glu Asp Glu Lys Asn Glu Ser
    50                  55                  60

Gly Leu Thr Glu Tyr Arg Leu Val Ser Ile Asn Lys Ser Ser Pro Leu
65                  70                  75                  80

Gln Lys Gln Leu Pro Ala Phe Ile Ser Glu Asp Ala Ser Gly Tyr Leu
                85                  90                  95

Thr Ser Ser Trp Leu Thr Leu Phe Val Pro Ser Val Tyr Thr Gly Val
            100                 105                 110

Phe Val Val Ser Leu Pro Leu Asn Ile Met Ala Ile Val Val Phe Ile
        115                 120                 125

Leu Lys Met Lys Val Lys Lys Pro Ala Val Val Tyr Met Leu His Leu
    130                 135                 140

Ala Thr Ala Asp Val Leu Phe Val Ser Val Leu Pro Phe Lys Ile Ser
145                 150                 155                 160

Tyr Tyr Phe Ser Gly Ser Asp Trp Gln Phe Gly Ser Glu Leu Cys Arg
                165                 170                 175
```

```
Phe Val Thr Ala Ala Phe Tyr Cys Asn Met Tyr Ala Ser Ile Leu Leu
            180             185                 190
Met Thr Val Ile Ser Ile Asp Arg Phe Leu Ala Val Val Tyr Pro Met
        195             200             205
Gln Ser Leu Ser Trp Arg Thr Leu Gly Arg Ala Ser Phe Thr Cys Leu
    210             215             220
Ala Ile Trp Ala Leu Ala Ile Ala Gly Val Val Pro Leu Val Leu Lys
225             230             235                         240
Glu Gln Thr Ile Gln Val Pro Gly Leu Asn Ile Thr Thr Cys His Asp
                245             250                     255
Val Leu Asn Glu Thr Leu Leu Glu Gly Tyr Tyr Ala Tyr Tyr Phe Ser
            260             265             270
Ala Phe Ser Ala Val Phe Phe Val Pro Leu Ile Ile Ser Thr Val
        275             280             285
Cys Tyr Val Ser Ile Ile Arg Cys Leu Ser Ser Ser Ala Val Ala Asn
    290             295             300
Arg Ser Lys Lys Ser Arg Ala Leu Phe Leu Ser Ala Ala Val Phe Cys
305             310             315                         320
Ile Phe Ile Ile Cys Phe Gly Pro Thr Asn Val Leu Leu Ile Ala His
                325             330                     335
Tyr Ser Phe Leu Ser His Thr Ser Thr Thr Glu Ala Ala Tyr Phe Ala
            340             345                 350
Tyr Leu Leu Cys Val Cys Val Ser Ser Ile Ser Ser Cys Ile Asp Pro
        355             360             365
Leu Ile Tyr Tyr Tyr Ala Ser Ser Glu Cys Gln Arg Tyr Val Tyr Ser
    370             375             380
Ile Leu Cys Cys Lys Glu Ser Ser Asp Pro Ser Ser Tyr Asn Ser Ser
385             390             395                         400
Gly Gln Leu Met Ala Ser Lys Met Asp Thr Cys Ser Ser Asn Leu Asn
            405             410                     415
Asn Ser Ile Tyr Lys Lys Leu Leu Thr
            420             425
```

RECOMBINANT THROMBIN RECEPTOR AND RELATED PHARMACEUTICALS

TECHNICAL FIELD

The invention relates to materials involved in the control of the cardiovascular system, and in particular to activities mediated by the thrombin receptor. More specifically, it concerns recombinant materials useful for production of the thrombin receptor, the receptor as a diagnostic tool, and therapeutic and diagnostic compositions relevant to the receptor.

BACKGROUND ART

Thrombin is a powerful factor in regulating the state of the cardiovascular system. It is clear that thrombin aids in the formation of blood clots by catalyzing the conversion of fibrinogen to fibrin, which is an integral part of most clots. In addition, thrombin is known to act directly on cells in the blood and in the interior blood vessel wall, and specifically to activate platelets to form clots. Thrombin-induced platelet activation is particularly important for arterial thrombus formation, a process that causes myocardial infarction and some forms of unstable angina and stroke. In addition, thrombin promotes inflammation and other cellular activities. Thrombin is chemotactic for monocytes, mitogenic for lymphocytes, and causes endothelial cells to express the neutrophil adhesive protein GMP-140 on their surfaces. Thrombin elicits platelet-derived growth factor from the endothelium and is a mitogen for mesenchymal cells.

Because thrombin is capable of direct activation of cells, it is assumed that at least one thrombin receptor exists. However, it has not been possible to detect the presence of thrombin receptor by traditional binding studies, since thrombin is capable of binding a large number of materials present on cells, and thus the background levels of binding are prohibitively high.

The thrombin-binding proteins that have been identified do not seem to function as transduction molecules (Gronke, R. S., et al., *J Biol Chem* (1987) 262:3030–3036; Okamura, T., et al., *J Biol Chem* (1978) 253:3435. Modified thrombins that are physiologically inactive seem to bind to platelets in the same way as thrombin itself. Thus, the binding sites identified by traditional binding studies may not be related to any thrombin receptor. Also, thrombin is a protease and if the receptor were proteolytically cleaved by the interaction with thrombin, the receptor's ability to bind thrombin would be decreased. All of the foregoing factors suggest that traditional binding studies in an effort to find a thrombin receptor might ultimately be unproductive.

While it has been assumed that a thrombin receptor might exist, it has been unclear, even from the studies conducted so far, whether proteolytic cleavage by thrombin is involved in its receptor activation. When thrombin is treated with reagents which covalently modify and render it proteolytically inactive, its ability to stimulate platelets is abolished (Berndt, M. C., et al., "Platelets in Biology and Pathology" (1981) Elsevier/North Holland Biomedical Press, pp. 43–74; Martin, B. M., et al., *Biochemistry* (1975) 14:1308–1314; Tollefsen, D. M., et al., *J Biol Chem* (1974) 249:2646–2651; Phillips, D. R., *Thrombin Diath Haemorrh* (1974) 32:207–215; Workman, E. F., et al., *J Biol Chem* (1977) 252:7118–7123; Greco, N. J., et al., *Blood* (1990) 75:1983–1990. The modified forms of thrombin described in the reports above contain bulky or charged moieties that occupy the active site and also obscure additional regions of the surface of thrombin that bind substrate (Bode, W., et al., *Embo J* (1989) 8:3467–3475). Some of the chemically-modified thrombins do not, in fact, block thrombin-induced platelet activation and one modified nonproteolytic thrombin which does block platelet activation, D-phenylalanyl-L-prolyl-L-arginyl chloromethyl ketone (PPACK) thrombin fails to bind substrate. Thus, it cannot be concluded that a lack of protease activity accounts for failure to activate platelets.

During the course of the work described in the present application, two groups have reported that messenger RNA prepared from thrombin-responsive cell lines, when microinjected into *Xenopus oocytes*, conferred thrombin responsiveness on the oocytes. The mRNA was prepared either from a hamster lung fibroblast cell line, CCL39 (Van Obberghen-Schilling, E., et al., *FEBS Letters* (1990) 262:330–334) or from human umbilical venous endothelial cells (Pipili-Synetos, E., et al., *Biochem Biophys Res Commun* (1990) 171:913–919).

The identification and characterization of the thrombin receptor, as described herein, permits the design of systems and substances which can regulate thrombosis in the cardiovascular system. In addition, new diagnostic reagents for assessing cardiovascular status are provided by this work.

DISCLOSURE OF THE INVENTION

The invention provides methods and materials useful in the regulation of the cardiovascular system in mammals. The isolation, recombinant production, and characterization of the thrombin receptor associated with surfaces of cells activated by thrombin permits effective regulation of these functions.

Thus, in one aspect, the invention is directed to recombinant materials associated with the production of thrombin receptor. These include, for example, transfected cells which can be cultured so as to display the thrombin receptor on their surfaces, and thus provide an assay system for the interaction of materials with native thrombin receptor. These cells, or peptides which represent relevant portions of the receptors, can be used as diagnostics to determine the level of thrombin in samples, as well as screening tools for candidate substances which affect thrombin activity in vivo.

In another aspect, the invention is directed to thrombin agonists which mimic the activated form of the extracellular portion of the receptor protein. These agonists are useful in encouraging blood clotting, for example, in localized application at internal bleeding sites of hemophiliacs. The agonists also mimic thrombin's ability to stimulate fibroblast proliferation and thus may be useful in promoting wound healing.

In still another aspect, the invention is directed to thrombin antagonists. A first group of antagonists comprises modified forms of agonist proteins which lack the essential features required for activation of the receptor. These antagonists bind to receptor, but do not activate it, thus preventing receptor activation by thrombin.

A second group of antagonists of the invention include mimics of the receptor which would ordinarily represent cleavage and thrombin-binding regions of the receptor, including noncleavable peptides and peptides with enhanced binding for thrombin. These peptides are capable of binding thrombin so as to diminish the levels of thrombin available for binding to receptor. They thus diminish or prevent thrombin-mediated events such as thrombin-induced platelet aggregation, fibrinogen clotting and cell proliferation.

A third group of antagonists blocks the binding of thrombin to its receptor by providing alternate anionic regions to replace those of the thrombin receptor. These antagonists are mimics of the thrombin binding portion of the receptor. They bind to thrombin, thereby preventing thrombin interaction with the intact receptor.

Conversely, alternate cationic regions which mimic those present in the thrombin ligand can be included in antagonists which occupy the binding region of the receptor and prevent binding of thrombin.

A fifth group of antagonists will include antibodies which are designed to bind specific regions of receptor protein. In general, these are monoclonal antibody preparations which are highly specific for any desired region. The antibodies of the invention are also useful in immunoassays for the receptor protein, for example in assessing successful expression of the gene in recombinant systems.

A sixth group of antagonists comprises modified forms of thrombin lacking proteolytic activity.

In another aspect, the invention is related to assay systems which utilize recombinant thrombin receptor to screen for agonists and antagonists. Some systems include the use of the agonist peptides to screen for antagonists which inhibit the agonistic effect.

Another aspect of the invention relates to the diagnosis of cardiovascular disease by detection, in the urine, of the peptide cleaved from the thrombin receptor when activated as a measure of thrombosis. Another diagnostic method included in the invention is visualization of activated forms of receptor and detecting clots in the body by localizing and imaging these targets in situ using antibodies specific to the activated receptor.

Additional aspects of the invention are directed to pharmaceutical compositions containing the compounds of the invention. The compounds of the invention which serve as antagonists to the activation of the thrombin receptor are useful as anticoagulants and are helpful in a variety of clinical indications including treatment of abrupt closure in the context of angioplasty, the treatment of restenosis in the context of angioplasty, the treatment of unstable angina, the treatment of myocardial infarction, and treatment of some forms of thrombotic or thromboembolytic stroke. The compounds of the invention can be used alone or in combination with other therapeutic agents such as urokinase and tPA.

BRIEF DESCRIPTION OF THE DRAWINGS

FIGS. 1A and B show the DNA and deduced amino acid sequence of a human thrombin receptor.

MODES OF CARRYING OUT THE INVENTION

Figure 1A:
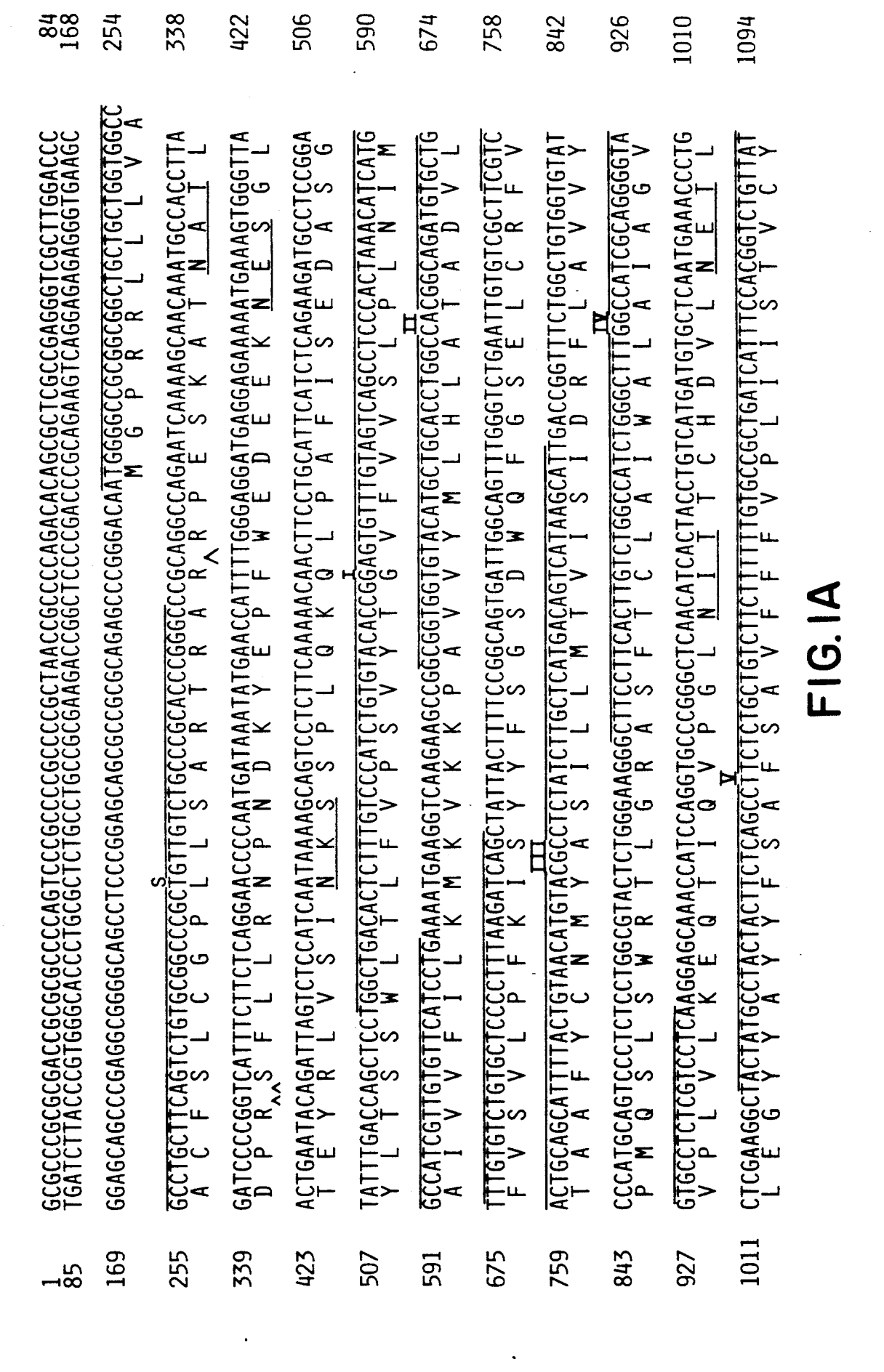
Figure 2:
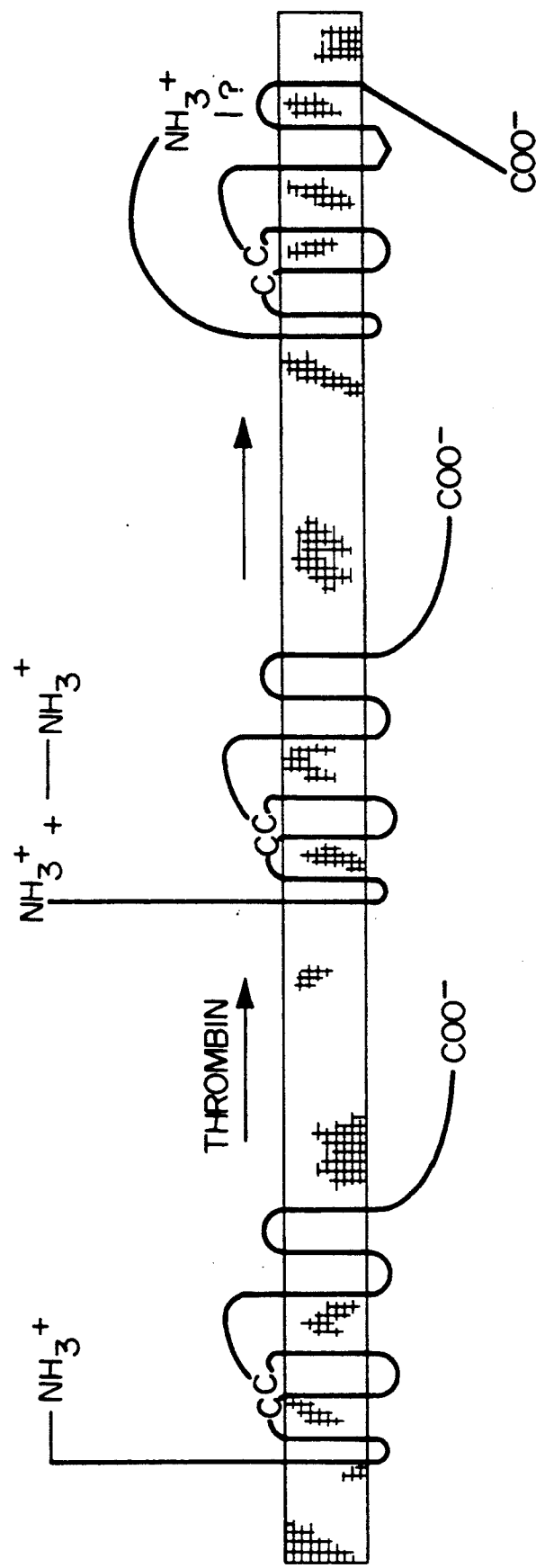
FIG. 2 shows a proposed model of thrombin receptor activation based on the deduced amino acid sequence.

The characteristics of the thrombin receptor elucidated by the invention herein are summarized in FIGS. 1A, 1B and 2. FIG. 1 shows the complete DNA sequence of the clone encoding the receptor along with the deduced amino acid sequence. The entire amino acid sequence contains 425 amino acids, including a 24 or 26 amino acid signal sequence which provides an approximately 400 amino acid mature receptor protein.

Hydrophobicity/hydrophilicity plots of the sequence shown in FIGS. 1A and B indicate that the mature receptor is a member of the 7-transmembrane domain receptor family and has a relatively long (approximately 75 amino acid) extracellular amino acid extension containing several consensus sites for asparagine-linked glycosylation. A disulfide bond linking cysteine-175 in the first extracellular loop with cysteine-254 in the second extracellular loop would be analogous to rhodopsin and $\beta$-2 adrenergic receptor. A proposed model of the in situ receptor is shown in FIG. 2.

Referring again to FIGS. 1A and B, the thrombin-catalyzed cleavage site is represented by the Arg-Ser linkage at positions 41 and 42. Cleavage at this site results in the liberation of a peptide fragment of the receptor designated an "activation peptide" extending from position 1 of the mature peptide to the cleavage site. The precise processing site of the receptor is not known and thus the N-terminus of the mature protein is somewhat uncertain. However, it is probably the arginine residue at position 28. The "activation peptide" would thus have the sequence RPESKATNATLDPR. The precise location of the N-terminus is unimportant for the design of the compounds of the invention. This "activation peptide" is expected to be filtered by the kidney and concentrated in the urine, and can be used as an index to platelet activation by thrombin.

The amino acid sequence destined to be cleaved by thrombin—i.e., the cleavage site—binds to thrombin's active site/"oxyanion hole" region which is contained in an extended binding pocket, designated an oxyanion-binding "exosite" which binds large substrates via hydrophobic, hydrogen bonding, and charge interactions. Typically, the sequence to be cleaved interacts with the amino acids of the active site, while sequences carboxyl to this cleavage site interact with the more extended anion binding exosites. The thrombin receptor contains the anionic sequence YEPFWEDEE at positions 52–60, as shown in FIGS. 1A and B. This region is just carboxyl to the cleavage site between positions 41 and 42. The location and the composition of this YEPFWEDEE sequence (aromatic/hydrophobic residues and anionic residues) strongly suggest that this sequence mediates thrombin binding to the receptor via thrombin's anion-binding exosite. This hypothesis is confirmed hereinbelow by showing that peptides representing this region of the receptor bind thrombin and inhibit its actions. This observation also predicts that polycationic substances that bind to this portion of the receptor may block thrombin binding and receptor activation.

Release of the activation peptide permits refolding of the receptor protein to activate the receptor. This is shown schematically in FIG. 2, which also shows that the conformational changes resulting from the liberation of the activation peptide and refolding results in an intracellular conformational change of the receptor. This hypothesis is confirmed by the finding that the thrombin receptor can be activated by a peptide mimicking the new amino terminus created by the activation. Accordingly, mimics of the N-terminus of the new amino terminus on the activated receptor behave as agonists therefor. The importance of the first two amino acids in the newly created amino terminus in the receptor for receptor activation has also been confirmed hereinbelow. Switching the positions of the amino terminal serine and phenylalanine results in complete loss of agonist activity for the above agonist peptides. Based on this information, and by analogy with the mechanisms underlying trypsinogen activation to trypsin, it appears that the positively charged amino group on serine that is newly exposed when thrombin cleaves the receptor plays an important role in receptor activation. Agonist peptides that bind the thrombin receptor but are modified to be lacking this amino group function as antagonists to the thrombin receptor. Thus, modifications of the agonist peptides which lack the capacity for specific activating interaction serve as antagonists.

Compounds of the Invention

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides shown, each gene-encoded residue, where appropriate, is represented by a single letter designation, corresponding to the trivial name of the amino acid, in accordance with the following conventional list:

| Amino Acid | One-Letter Symbol | Three-letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (†).

The compounds of the invention are peptides which are partially defined in terms of amino acid residues of designated classes. Amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.

Acidic: Aspartic acid and Glutamic acid;

Basic/noncyclic: Arginine, Lysine;
Basic/cyclic: Histidine;
Neutral/polar/small: Glycine, serine, cysteine;
Neutral/nonpolar/small: Alanine;
Neutral/polar/large/nonaromatic: Threonine, Asparagine, Glutamine;
Neutral/polar/large aromatic: Tyrosine;
Neutral/nonpolar/large/nonaromatic: Valine, Isoleucine, Leucine, Methionine;
Neutral/nonpolar/large/aromatic: Phenylalanine, and Tryptophan.

The gene-encoded amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (beta-ala), or other omega-amino acids, such as 3-amino propionic, 4-amino butyric and so forth, alpha-aminoisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) and methionine sulfoxide (MSO). These also fall conveniently into particular categories.

Based on the above definitions,
Sar and beta-ala and Aib are neutral/nonpolar/small;
t-BuA, t-BuG, N-MeIle, Nle and Cha are neutral/nonpolar/large/nonaromatic;
Orn is basic/noncyclic;
Cya is acidic;
Cit, Acetyl Lys, and MSO are neutral/polar/large/nonaromatic; and
Phg is neutral/nonpolar/large/aromatic.

The various omega-amino acids are classified according to size as neutral/nonpolar/small (beta-ala, i.e., 3-aminopropionic, 4-aminobutyric) or large (all others).

Other amino acid substitutions of those encoded in the gene can also be included in peptide compounds within the scope of the invention and can be classified within this general scheme.

A. Agonists

The agonists of the invention comprise a series of peptides of the formula

$$AA_x-AA_y-(AA_i)_n-Z \quad (1)$$

wherein $AA_x$ is selected from ser, ala and gly and $AA_y$ is an aromatic amino acid residue;

wherein AA represents an amino acid residue and the subscript i is an integer which denotes the position of the referent amino acid residue downstream (N→C) of the $AA_y$ residue of formula (1), and n is an integer of 1–12; and wherein $AA_1$ and $AA_2$ are each independently neutral/nonpolar/large/nonaromatic amino acid residues;

$AA_3$ and $AA_8$ are each independently basic amino acid residues;

$AA_4$ and $AA_6$ are each independently neutral/polar/large/nonaromatic amino acids;

$AA_5$ and $AA_{11}$ are proline residues;

$AA_7$ and $AA_{10}$ are each independently acidic amino acid residues; and $AA_9$ and $AA_{12}$ are each independently neutral/aromatic amino acid residues.

The peptide of formula 1 can be extended (shown as Z) at the C-terminus (but not the N-terminus) by noninterfering substituents.

At the C-terminus of the compounds of formula 1, the carboxyl group may be in the underivatized form or may be amidated; in the underivatized form the carboxyl may be as a free acid or a salt, preferably a pharmaceutically acceptable salt.

If the C-terminus is amidated, the nitrogen atom of the amido group, covalently bound to the carbonyl carbon at the C-terminus, will be $-NH_2$, $-NHR$, or $NRR'$, wherein R and R' are straight or branched chain alkyl of 1-6C, such alkyls are 1-6C straight- or branched-chain saturated hydrocarbyl residues, such as methyl, ethyl, isopentyl, n-hexyl, and the like. Representatives of such amido groups are: $-NH_2$, $-NHCH_3$, $-N(CH_3)_2$, $-NHCH_2CH_3$, $-NHCH_2CH(CH_3)_2$, and $-NHCH_2CH(CH_3)CH_2CH_3$, among others.

Preferred embodiments of $AA_x-AA_y$ include GF, AF, SF, GW, AW, SW, GY, AY and SY. Preferred embodiments for the residues in the remainder of the compound of formula (1) are those wherein $AA_1$ and $AA_2$ are each independently leu, val or ile; or $AA_3$ and $AA_8$ are each independently arg or lys; or $AA_4$ and $AA_6$ are each independently gln or asn; or $AA_7$ and $AA_{10}$ are each independently asp or glu; or $AA_{12}$ is phe and $AA_9$ is tyr; or Z is OH, $NH_2$, NHR or NRR' wherein R and R' are straight or branched chain alkyl of 1-6C; or Z includes some or all of $AA_{13}-AA_{17}$ as defined below. Particularly preferred are compounds of formula (1) which are selected from the group consisting of SFLLRNPNDKYEPF; SPLLRNPNDKYEP; SFLLRNPNDKYE; SFLLRNPNDKY; SFLLRNPNDK; SFLLRNPD; SFLLRNPN; SFLLRNP; SFLLRN; SFLLR; SFLL; and SFL, and the amidated forms thereof.

B. Antagonists

Compounds of the invention which interfere with platelet activation and other cellular activities mediated by the thrombin acceptor include the following:

1) Antagonists for the thrombin receptor which represent modified agonist peptides lacking the N-terminal serine;

2) Antagonists which represent noncleavable and/or enhanced binding forms of the extracellular portions of the thrombin receptor which behave as decoys for the circulating thrombin;

3) Anionic and hydrophobic/anionic peptides which mimic the YEPFWEDEE oxyanionic exosite-binding region and which also behave as decoys for circulating thrombin;

4) Cationic or extended cationic peptides which mimic the oxyanionic exosite of thrombin itself and bind to the receptor in competition with thrombin;

5) Antibodies which are immunoreactive with various critical positions on the thrombin receptor; and 6) Thrombin mutants lacking proteolytic activity which compete with native thrombin for the receptor.

Antagonists Which are Modified Agonist Peptides

With respect to the antagonists of either groups 1) or 2), these are of the formula

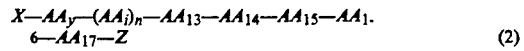

$$X-AA_y-(AA_i)_n-AA_{13}-AA_{14}-AA_{15}-AA_{16}-AA_{17}-Z \quad (2)$$

wherein $AA_y$ is an aromatic amino acid residue, and
wherein AA represents an amino acid residue and the subscript i is an integer which denotes the position of the referent amino acid residue downstream (N→C) of the AA$_y$ residue of formula (2) and n is an integer of 1-12; and wherein AA$_1$ and AA$_2$ are each independently neutral/nonpolar/large/nonaromatic amino acid residues;

AA$_3$ and AA$_8$ are each independently basic amino acid residues;

AA$_4$ and AA$_6$ are each independently neutral/polar/large/nonaromatic amino acids;

AA$_5$ and AA$_{11}$ are proline residues;

AA$_7$ and AA$_{10}$ are each independently acidic amino acid residues;

AA$_9$ and AA$_{12}$ are each independently neutral/aromatic amino acid residues; and wherein all of, or a C-terminal portion of, AA$_{1-3}$-AA$_{17}$ may be present or absent and wherein AA$_{13}$ when present is a neutral/aromatic amino acid residue or a small amino acid residue and wherein AA$_{14}$-AA$_{17}$ when present are each independently acidic amino acid residues or neutral/polar/large/nonaromatic amino acid residues; and wherein X is an amino acid residue other than ser, ala or gly or is a desamino or acylated amino acid, or wherein X is a peptide extension of 2-5 amino acids or an acylated form thereof; and Z is a noninterfering substituent.

As above, preferred embodiments include those wherein AA$_1$ and AA$_2$ are each independently leu, val or ile; or AA$_3$ and AA$_8$ are each independently arg or lys; or AA$_4$ and AA$_6$ are each independently gln or asn; or AA$_7$ and AA$_{10}$ are each independently asp or glu; or AA$_{12}$ is phe and AA$_9$ is tyr; or Z is OH, NH$_2$, NHR or NRR' wherein R and R' are straight or branched chain alkyl of 1-6C.

Preferred embodiments of AA$_{13}$-AA$_{17}$ are those wherein AA$_{13}$ is trp, phe or ala; or AA$_{14}$AA$_{17}$ are each independently selected from glu, asp or gln, especially wherein AA$_{13}$-Aa$_{17}$ is of the formula WEDEE, WQDQQ, WEDEQ, WQDEQ, WQDEE, WEDQE, WEDQQ OR WQDQE.

Preferred embodiments of X include L-D-P-R-P; F$^\dagger$-P-R-P, desaminoserine, and a proline residue. In more detail when X is a single amino acid residue other than ser, gly or ala, or a single amino acid residue in its des-amino form, or a single amino acid residue in acylated form, those embodiments wherein X is lys or arg are preferred. When X is a peptide extension of 2-5 amino acid residues or an acylated or desamino form thereof, the compounds of formula (2) are preferred wherein said peptide extension includes the sequence PRP at its C-terminus, optionally further including an N-terminal sequence comprising a large/nonaromatic/nonpolar/neutral amino acid residue conjugated through a peptide bond to an acidic amino acid residue, especially wherein said peptide extension represented by X is selected from the group consisting of LDPRP, LEPRP, IDPRP, IEPRP, VDPRP and VEPRP. Also preferred are those wherein PRP is preceded by a D amino acid, especially phe or trp. Particularly preferred are peptides which are selected from the group consisting of LDPRPFLLRNPNDKYEPFWEDEEKNES; LDPRPFLLRNPNDKYEPFWEDEEKNE; LDPRPFLLRNPNDKYEPFWEDEEKN; LDPRPFLLRNPNDKYEPFWEDEEK; LDPRPFLLRNPNDKYEPFWEDEE; LDPRPFLLRNPNDKYEPFWEDE; and LDPRPFLLRNPNDKYEPFWED, and the amidated or acylated forms thereof. Also preferred are those which are selected from the group consisting of F$^\dagger$PRPFLLRNPNDKYEPFWEDEEKNES, F$^\dagger$PRPFLLRNPNDKYEPFWEDEEKNE, F$^\dagger$PRPFLLRNPNDKYUEPFWEDEEKN, F$^\dagger$PRPFLLRNPNDKYEPFWEDEEK, F$^\dagger$PRPFLLRNPNDKYEPFWEDEE, F$^\dagger$PRPFLLRNPNDKYUEPFWEDE, and F$^\dagger$PRPFLLRNPNDKYEPFWED, and F$^\dagger$PRPFLLRNPNDKYEPFWEDEEKNES, F$^\dagger$PRPFLRNPNDKYEPFWEDEEKNES, F$^\dagger$PRPFRNPNDKYEPFWEDEEKNES, F$^\dagger$PRPFNPNDKYEPFWEDEEKNES, F$^\dagger$PRPFPNDKYEPFWEDEEKNES, F$^\dagger$PRPFNDKYEPFWEDEEKNES, F$^\dagger$PRPFDKYEPFWEDEEKNES, F$^\dagger$PRPFKYEPFWEDEEKNES, F$^\dagger$PRPFYEPFWEDEEKNES, F$^\dagger$PRPFEPFWEDEEKNES, F$^\dagger$PRPFPFWEDEEKNES and F$^\dagger$PRPFFWEDEEKNES, and the amidated and acylated forms thereof.

Oxyanion Exosite-Binding Antagonists

Antagonists which represent anionic peptides mimicking the YEPFWEDEE box (group 3) are represented by the formula:

$$Y-AA_{13}-AA_{14}-AA_{15}-AA_{16}-AA_{17}-Z \qquad (3)$$

wherein AA$_{13}$ through AA$_{17}$ are as above defined, and wherein Y and Z are noninterfering substituents, typically peptide extensions, but can also include noninterfering organic radicals in general. Y can also be H or acyl; Z may also be OH or NH$_2$, NHR, or NRR', as set forth hereinabove.

Preferred forms of compounds of formula (3) are those wherein AA$_{13}$ is phe, trp or ala; or AA$_{14}$-AA$_{17}$ are each independently selected from the group consisting of glu, asp and gln; or AA$_{14}$-AA$_{17}$ is of the sequence WEDEE, WQDQQ, WEDEQ, WQDEQ, WQDEE, WEDQE, WEDQQ OR WQDQE. Preferred embodiments of Y include those wherein Y is a peptide extension of 1-4 amino acids or the acylated form thereof. Especially preferred are those wherein said peptide extension is of the formula AA$_f$—AA$_g$—AA$_h$—AA$_j$, wherein AA$_f$ and AA$_h$ are each independently aromatic amino acid residues or small nonaromatic residues, AA$_g$ is acidic or large/polar/nonaromatic amino acid residue and AA$_h$ is a small amino acid residue or proline.

These antagonists serve as decoys for thrombin, thus lowering its effective concentration.

Oxyanionic-Binding Exosite Mimics

The cationic peptides mimicking the oxyanionic-binding exosite of thrombin (group 4) are of the formula:

$$Y-AA_1-AA_b-AA_c-AA_d-AA_e-A \qquad (4)$$

wherein Y and Z are defined as above, and wherein AA$_a$ and AA$_e$ are each independently hydrophobic amino acids or basic amino acids, and where each of AA$_b$, AA$_c$, and AA$_d$ is independently a basic amino acid.

Preferred are compounds of formula (4) wherein Y is acyl or H; or Z is OH, NH$_2$, NHR or NRR' wherein R and R' are straight or branched chain alkyl of 1-6C; or AA$_a$ and AA$_e$ are each independently selected from phe, trp and ala; or AA$_b$-AA$_d$ are each independently selected from the group consisting of arg, lys and gln;

especially wherein $AA_a$–$AA_e$ has the sequence WKKKK, KKKKW, QKQQW, or WQKQQ.

The noninterfering substituents represented by Y and Z may be further peptide extensions which are compatible with the binding pattern of the thrombin oxyanionic-binding exosite. As they mimic this capacity of thrombin to bind its substrate, these antagonists are operative by virtue of their ability to bind the relevant regions of the thrombin receptor protein, and, in particular, the region YEPFWEDEE at positions 52-60, as shown in FIGS. 1A and B.

Antibodies

Antagonists which are antibodies immunoreactive with critical positions of the thrombin receptor (group 5) are obtained by immunization of suitable mammalian subjects with peptides containing as antigenic regions those portions of the thrombin receptor intended to be targeted by the antibodies. Critical regions include the region of proteolytic cleavage, the binding site at the YEPFWEDEE box, the segment of the extracellular segment critical for activation (this includes the cleavage site), and the portions of the sequence which form the extracellular loops, in particular, that region which interacts with the N-terminus of the activated receptor extracellular region. The agonist peptides of the invention may be used as immunogens in this case.

Thus, suitable peptides to use as immunogens to prepare the desired antibodies include those peptides representing portions of the mature sequence of the extracellular region from positions 28 to position 60 at the C-terminal end of the YEPFWEDEE box, especially peptides which include the sequence LDPRSFLL (which includes the cleavage site) and YEPFWEDEE (which includes the binding site. Alternative regions which are useful as immunogens include the segment representing amino acids 161-176; 240-265; and 336-346. These peptides of the sequences, respectively, YYFSGSDWQFGSELCR, KEQTIQVPGLNITTCHDVLNETLLEG, and HYSFLSHTSTT, represent the proposed extracellular loops.

The antibodies are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the thrombin receptor itself displayed on a recombinant host cell. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

Noncleavable Thrombin

In addition to the foregoing, antagonists comprise thrombin mutants lacking proteolytic activity that compete with native thrombin for the receptor (group 6). As set forth above, it is understood that the participants in the proteolytic cleavage site of thrombin include the serine residue at position 205, the histidine residue at position 57, and the aspartic acid residue at position 99. Mutants of thrombin containing replacements for these residues which render the thrombin molecule proteolytically inactive are prepared using standard site-directed mutagenesis techniques, and the mutant genes used to produce the modified thrombin using recombinant techniques. The relevant substitutions are denoted by the position number preceded by the native residue and followed by the substituted residue. Thus, thrombin with serine at position 205 replaced by alanine is denoted S205A.

Preferred Embodiments

In both the agonists and antagonists of groups (1)–(4) of the invention, preferred embodiments of the amino acid sequences are those wherein the amino acid in the peptides are those encoded by the gene. Also included are those wherein only one or two of the amino acid residues is replaced by one which is not encoded genetically.

In more detail, preferred embodiments of $AA_1$ and $AA_2$ are leu, val, or ile; especially preferred is leu. Preferred embodiments of $AA_3$ and $AA_8$ are arg or lys; especially preferred are embodiments wherein $AA_3$ is arg and $AA_8$ is lys. Preferred embodiments for $AA_4$ and $AA_6$ are gln or asn, and especially asn. Preferred embodiments for $AA_7$ and $AA_{10}$ are asp or glu; particularly preferred are embodiments wherein $AA_7$ is asp and $AA_{10}$ is glu. A preferred embodiment for $AA_{12}$ is phenylalanine, and of $AA_9$ is tyrosine.

With respect to the embodiments of X in the antagonist peptides, particularly preferred embodiments are those wherein X is des-aminoser, acyl-ser or a single amino acid other than serine, glycine or alanine and larger than 4 carbons, inclusive of the carboxyl, or said alternate amino acid lacking an α-amino group, or having an acylated amino group. Particularly preferred among these amino acids are basic amino acids, particularly lysine and arginine, and most preferably arginine. These embodiments of X represent the antagonists of group (1) wherein the agonist N terminus is altered to delete the serine residue. Particularly preferred among the agonist peptides of this class are those selected from the group consisting of XFLLRNPNDKYEPF; XFLLRNPNDKYEP; XFLLRNPNDKYE;

XFLLRNPNDKY; XFLLRNPNDK; XFLLRNPND; XFLLRNPN; XFLLRNP; XFLLRN; XFLLR; XFLL; and XFL, wherein X is a single amino acid other than serine, glycine or alanine or a desamino form thereof. Preferred embodiments of Z include those containing all, or the upstream portion, of $AA_{13}$-$AA_{17}$ as in the antagonists of group (2).

For those antagonists of group (2), wherein the peptide mimics the thrombin receptor extracellular chain but lacks a proteolytic site and/or has enhanced binding for thrombin, particularly preferred embodiments are those which include amino acid residues $AA_{13}$-$AA_{17}$ or a fragment thereof and wherein X is a peptide extension of 4–5 amino acid residues. Particularly preferred are those wherein the residues immediately upstream of $AA_y$ have the sequence pro-arg-pro (PRP) preceded by residues selected from the group consisting of dipeptide sequences consisting of a large, nonaromatic, nonpolar neutral amino acid residue conjugated through a peptide bond to an acidic amino acid residue downstream. Particularly preferred embodiments of this dipeptide sequence are ile-asp, val-asp, ile-glu, and leu-asp.

In addition, where the peptide extension includes the immediately upstream sequence pro-arg-pro, an additional preferred upstream further extension is a D amino acid. Particularly preferred are D amino acids which are large/nonpolar/neutral/aromatic, particularly tryptophan or phenylalanine, and in particular phenylalanine.

Preferred embodiments of $AA_{13}$-$AA_{17}$ in the antagonists above are those wherein $AA_{13}$ is alanine, tyrosine, tryptophan or phenylalanine, preferably tryptophan, and wherein $AA_{14}$-$AA_{17}$ are independently selected from glu, asp, and asn.

For the antagonists of group (3) of formula (3) similar preferences for $AA_{13}$-$AA_{17}$ pertain.

Preferred embodiments of the antagonists of formula (4) are those wherein $AA_a$ and $AA_e$ are each independently tyrosine, phenylalanine, alanine, or tryptophan and $AA_b$-$AA_d$ are independently arginine or lysine residues. Most preferred are those embodiments wherein only one of $AA_a$ and $AA_e$ is aromatic, and the remaining amino acids are lysine.

Preferred acyl groups are of the formula RCO— wherein R represents a straight or branched chain alkyl of 1–6C. Acetyl is particularly preferred.

In all of the peptides of the invention, one or more amide linkages (—CO—NH—) may optionally be replaced with another linkage which is an isostere such as —$CH_2NH$—, —$CH_2S$—, —$CH_2CH_2$, —CH=CH— (cis and trans), —$COCH_2$—, —$CH(OH)CH_2$— and —$CH_2SO$—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—$CH_2NH$—, —$CH_2CH_2$—); Spatola, A. F., et al., *Life Sci* (1986) 38:1243–1249 (—$CH_2$—S); Hann, M. M., *J Chem Soc Perkin Trans I* (1982) 307–314 (—CH—CH—, cis and trans); Almquist, R. G., et al., *J Med Chem* (1980) 23:1392–1398 (—$COCH_2$—); Jennings-White, C., et al., *Tetrahedron Lett* (1982) 23:2533 (—$COCH_2$—); Szelke, M., et al., European Application EP 45665 (1982) CA:97:39405 (1982) (—$CH(OH)CH_2$—); Holladay, M. W., et al., *Tetrahedron Lett* (1983) 24:4401–4404 (—$C(OH)CH_2$—); and Hruby, V. J., *Life Sci* (1982) 31:189–199 (—$CH_2$—S—).

Preparation of Peptide Agonists and Antagonists

The peptide agonists and antagonists of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Recombinant Production of Thrombin Receptor

The invention provides recombinant materials for the production of thrombin receptor for display on the surface of recombinant cells. Production of the receptor using these recombinant methods provides a useful diagnostic reagent either to determine the level of thrombin in biological samples or, more importantly, as a reagent to screen candidate substances which affect thrombin activity.

For this recombinant production, a DNA sequence encoding the thrombin receptor, as set forth in FIG. 1, or its degenerate analogs is prepared either by retrieval of the native sequence, as set forth below, or by using substantial portions of the known native sequence as probe, or can be synthesized de novo using standard procedures. The DNA is ligated into expression vectors suitable for the desired transformed host and transformed into compatible cells. The cells are cultured under conditions which favor the expression of the thrombin receptor encoding gene and the cells displaying the receptor on the surface harvested.

Use of Recombinant Thrombin Receptor as a Diagnostic and Screening Tool

The availability of the recombinant DNA encoding thrombin receptor permits expression of the receptor on host cell surfaces, thus making the cells available as a tool for evaluating the ability of candidate agonists or antagonists to bind to receptor.

In one type of easily conducted assay, competition of a candidate antagonist for binding to the receptor with either labeled thrombin, a thrombin agonist or known binding antagonist can be tested. The labeled substance known to bind the receptor can, of course, be a synthetic peptide. Varying concentrations of the candidate are supplied along with a constant concentration of labeled thrombin, thrombin agonist, or antagonist, and the inhibition of a binding of label to the receptor can be evaluated using known techniques.

In a somewhat more sophisticated approach, the effect of candidate compounds on thrombin-induced responses can be measured in the cells recombinantly expressing the thrombin receptor as described below. Assay systems for the effect of thrombin on these cells include calcium mobilization and voltage clamp which are further described in detail hereinbelow. Other suitable endpoints include thrombin-induced phosphoinositol turnover and inhibition of adenyl cyclase. These assays permit an assessment of the effect of the candidate antagonist on the receptor activity rather than simply ability to bind to thrombin.

Diagnosis of Cardiovascular Disease

In one embodiment, the availability of the recombinant thrombin receptor protein permits production of antibodies which are immunospecific to the activated form of the receptor which can then be used for diagnostic imaging of activated receptors in vivo. These antibodies are produced either to the activated form of the receptor produced recombinantly, or to the peptide representing the "new amino terminal" peptide described in Example 2 below. The resulting antibodies, or the immunospecific fragments thereof, such as the Fab, Fab', Fab'$_2$ fragments are then conjugated to labels which are detected by known methods, such as radiolabels including technetium$^{99}$ and indium$^{111}$ or other radioactive labels as is known in the art. When injected in vivo. These antibodies home to the sites of activated receptor, thus permitting localization of problem areas which are subject to thrombosis.

In another embodiment of diagnosis, the presence of the activation peptide in body fluids can be detected and measured. Antibodies are made to the activation peptide as described above and can be employed in standard ELISA or RIA assays to detect excess amounts of the activation peptide in, for example, urine.

Utility and Administration of Antagonists

The antagonists of the invention are useful therapeutically in the treatment of abrupt closure or restinosis in the context of angioplasty; in the treatment of unstable angina; and in the treatment of myocardial infarction. The peptides of the invention which behave as antagonists are administered in conventional formulations for systemic administration as is known in the art. Typical such formulations may be found, for example, in *Remington's Pharmaceutical Sciences*, Mack Publishing Co., Easton Pa., latest edition.

Preferred forms of systemic administration of peptides include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents, In addition, if properly formulated in enteric or encapsulated formulations, oral administration may also be possible.

The dosage range required depends on the choice of antagonist, the route of administration, the nature of the formulation, the nature of the patient's illness, and the judgment of the attending physician. Suitable dosage ranges, however, are in the range of 0.1–100 μg/kg of subject. Wide variations in the needed dosage, however, are to be expected in view of the variety of antagonists available and the differing efficiencies of various routes of administration. For example, oral administration would be expected to require higher dosages than administration by intravenous injection. Variations in these dosage levels can be adjusted using standard empirical routines for optimization as is well understood in the art.

The agonists of the invention are useful in the treatment of wounds and in other contexts wherein fibroblast proliferation is useful. Administration of these compounds is generally topical and/or localized, in the form of salves, pastes, gels and the like.

Assay Systems

Calcium Mobilization: Agonist-induced increases in $^{45}$Ca release by oocytes expressing cRNA encoding thrombin receptor were assessed by published techniques (Williams, J. A., et al., *Proc Natl Acad Sci* U.S.A. (1988) 85:4939–4943). Briefly, intracellular calcium pools are labeled by incubating groups of 30 oocytes in 300 μl calcium-free MBSH containing 50 μCi $^{45}$CaCl$_2$ (10–40 mCi/mg Ca; Amersham) for 4 hours at RT. The labeled oocytes are washed, then incubated in MBSH II without antibiotics for 90 minutes. Groups of 5 oocytes are selected and placed in individual wells in a 24-well tissue culture plate (Falcon 3047) containing 0.5 ml/well MBSH II without antibiotics. This medium is removed and replaced with fresh medium every 10 minutes; the harvested medium is analyzed by scintillation counting to determine $^{45}$Ca released by the oocytes during each 10-minute incubation. The 10-minute incubations are continued until a stable baseline of $^{45}$Ca release per unit time is achieved. Two additional 10-minute collections are obtained, then test medium including agonist is added and agonist-induced $^{45}$Ca release determined.

Voltage Clamp: Agonist-induced inward chloride currents are measured in voltage-clamped oocytes expressing thrombin receptor encoding cRNA essentially as previously described (Julius, D., et al, *Science* (1988) 241:558–563) except that the single electrode voltage-clamp technique is employed.

The following examples are intended to illustrate but not to limit the invention.

EXAMPLE 1

Preparation of cDNA Encoding Thrombin Receptor

In summary, the human cell lines HEL (Papayannopoulou, T., et al., *J Clin Invest* (1987) 79:859–866) and Dami cells (Greenberg, S. M., et al., *Blood* (1988) 72:1968–1977) were stimulated with phorbol 12-myristate 13-acetate (PMA) before isolation of mRNA for microinjection into *Xenopus oocytes*. The oocytes which had been injected with these mRNA samples were then assayed for cellular calcium mobilization to detect those eggs which were expressing the thrombin receptor encoded by the RNA at their surfaces. After size selection of the mRNA, a 40 kb mRNA fraction was used for preparation of a cDNA library. The library was assayed by conversion of plasmid DNA, cloned in *E. coli*, into capped cRNA in an in vitro system, and injection of the capped cRNA into the oocytes. An insert in a positive clone was sequenced to obtain the cDNA and deduced amino acid sequence shown in FIG. 1.

In more detail, Xenopus oocytes were harvested from female *Xenopus laevis* and processed using published techniques (Coleman, A., in Hames, B. D., and Higgins, S. J., eds., *Transcription and Translation: A Practical Approach*. IRL Press, pp. 271–302; Williams, J. A., et al., *Proc Natl Acad Sci* U.S.A. (1988) 85:4939–4943). To remove follicular cells, oocytes were incubated for 4 hours at RT with 1 mg/ml Sigma type II collagenase in modified Barth's solution (MBSH) without calcium, then washed and incubated overnight at 18° C. in MBSH II (MBSH containing 1 mg/ml bovine serum albumin, 1 mg/ml Ficoll, 100 U/ml penicillin, 100 μl/ml streptomycin, and 50 μg/ml gentamicin).

Dumont stage V oocytes were selected and microinjected with 50 ml of the mRNA to be tested (1 μg/1 in 10 mM Hepes, pH 7.0); 5 ng of cRNA transcribed from a cDNA encoding a secreted form of alkaline phosphatase (generously provided by Dr. S. Udenfriend) was coinjected with all mRNA or cRNA samples as an internal standard for selection of healthy oocytes (Tate, S. S., et al., *FASEB J* (1990) 1:227–231). Microinjected oocytes were cultured for 48 h at 18° C. in MBSH II in individual wells in 96-well culture plates; the oocyte-conditioned medium was then assayed for alkaline phosphatase activity as described (Tate et al., (supra)) and the "best-expressing" oocytes were selected for functional assays.

Cytoplasmic and poly A+ RNA were prepared from HEL and Dami cells by standard techniques (Sambrook, J., et al., *Molecular Cloning*, 1989, Cold Spring Harbor Laboratory Press, New York). Poly A+ RNA was fractionated by size by centrifugation through a 10–30% sucrose density gradient exactly as described by Sumikawa, K., et al., *Nucl Acids Res* (1982) 10:5809–5822. Aliquots of each gradient fraction were analyzed for size by glyoxal gel electrophoresis. The remainder of each fraction was twice ethanol precipitated, and RNA dissolved at 1 µg/µl in 10 mM Hepes, pH 7.0. Aliquots of each fraction were assayed in the oocyte system described above for thrombin receptor activity.

A size-selected cDNA library was synthesized from the 4 kb mRNA fraction enriched for thrombin receptor activity using the method of Gubler and Hoffman (*Gene* (1983) 25:263–269). After ligation to BstXI adapters (Aruffo and Seed, *Proc Natl Acad Sci* U.S.A. (1987) 84:8573–8577), cDNAs of approximately 3.5 kb or greater were selected by acrylamide gel electrophoresis prior to ligation into the cloning vector pFROG. The pFROG vector was derived from pCDM6XL (a pH4M-derived vector (Aruffo and Seed (supra)) generously provided by C. Spencer Yost, UCSF) by adding a linker inserting a restriction site for the rare cutter MluI next to the NotI site. pFROG placed the cDNA under the transcriptional control of the SP6 RNA polymerase promoter and directed the synthesis of a hybrid mRNA containing the 5'-untranslated region of Xenopus globin followed by message encoded by the cDNA insert.

The *E. coli* strain MC1061 was transformed with the cDNA library by electroporation, and plated in 50 pools of 20,000 clones per pool. MC1061 carrying a model clone, serotonin 1c receptor cDNA in pFROG, was included at one clone per 2000 as an internal standard. Plasmid DNA was prepared from each pool and made linear by digestion with NotI; capped cRNA was produced in vitro (Krieg and Melton, *Meth Enzymol* (1987) 155:397–415) and assayed for thrombin receptor activity in the oocyte system as described above.

All pools were screened using both the voltage clamp and $^{45}$Ca release assay. Of the first five pools screened, all showed some thrombin receptor activity; in the $^{45}$Ca release assay, thrombin-induced increases in $^{45}$Ca release ranged from two- to sixfold. The most active pool was replated at approximately 2000 clones per plate and rescreened in the oocyte system. Two of 10 pools screened were positive for thrombin receptor activity. The most active of these was replated at 300 clones per plate and the pools rescreened. By progressive selection and subdivision of active pools, a single clone was identified.

The 3480-nucleotide cDNA insert was subcloned into the XhoI site of pBluescript. Restriction fragments of the insert were subcloned into M13. The cDNA sequence was determined twice in each direction (three times for the coding region) by dideoxy sequencing. The results are shown in FIGS. 1A and B.

FIGS. 1A and B show both the nucleotide sequence and the deduced amino acid sequence for the thrombin receptor protein. Hydrophobic regions, including a putative signal sequence and seven transmembrane spans are overlined. After processing of the signal sequence by signal peptidase, it is probable that additional processing by proline-directed arginyl cleavage occurs between the arginines at positions 27 and 28, which is marked on the Figures. Thus, the amino terminus of the mature protein begins RPESK.... Possible asparagine-linked glycosylation sites are underlined, and consensus polyadenylation regions are in bold. The putative thrombin receptor cleavage site at position $R_{41}/S_{42}$ is also marked.

As set forth above, FIG. 2 provides a diagram of the disposition of the thrombin receptor in the cell membrane. As shown in FIG. 2, the amino terminal extracellular extension of the intact and unactivated thrombin receptor is cleaved by thrombin, exposing a new amino terminus and releasing the short receptor fragment designated the "activation peptide" herein. The newly exposed amino terminus then functions as an agonist, binding to an as yet undefined region of the thrombin receptor and activating it. The thrombin receptor is thus activated by a mechanism analogous to zymogen-enzyme conversion. Thus, the thrombin receptor, like other receptors which contain seven transmembrane regions, contains its own ligand with the N-terminus in the native form of $S_{42}/F_{43}$.

EXAMPLE 2

Agonist Activity the "New Amino-Terminal" Peptide On Oocytes Expressing Wild-Type and Mutant Thrombin Receptor cRNA Oocytes were microinjected with 5 ng wild-type thrombin receptor cRNA (WT) or with 5 ng cRNA encoding a mutant thrombin receptor with the amino acid substitution R41A (R41A). The notation is analogous to that for thrombin as set forth above—alanine replaces arginine at position 41. Uninjected oocytes or oocytes expressing thrombin receptor cRNAs were then cultured for 48 hr and thrombin or peptide-induced $^{45}$Ca release determined as described above. Candidate agonists were added at saturating concentrations: thrombin at 250 pM and the "new amino-terminal" peptide SFLLRNPNDKYEPF (SFLL) at 25 µM. The control peptide FSLLRNPNDKYEPF (FSLL) was added at 100 µM. The data shown in Table 1 represent the mean +/− SEM of three replicate determinations; these results are representative of those obtained in three or four separate experiments.

TABLE 1

| Receptor | Agonist | Fold increase in $^{45}$Ca |
|---|---|---|
| WT | Thrombin | 26 |
| WT | SFLL 40 µM | 32 |
| WT | SFLL 200 µM | 42 |
| R41A | Thrombin | 0 |
| R41A | SFLL 200 µM | 53 |

The agonist peptide SFLL has no activity on uninjected oocytes (not shown). Qualitatively identical results were obtained when agonist-induced inward current in agonist-induced $^{45}$Ca release.

EXAMPLE 3

Agonist Function of the "New Amino-Terminal" Peptide for Platelet Secretion and Aggregation and Mitogenic Effects Washed human platelets were prepared as described by Baenzinger, N. G., *Meth Enz* (1974) 31:149-155; and Charo, I. F., et al., *J Clin Invest* (1977) 63:866-873. Agonist-induced responses were assessed as described above.

Figure 3A:
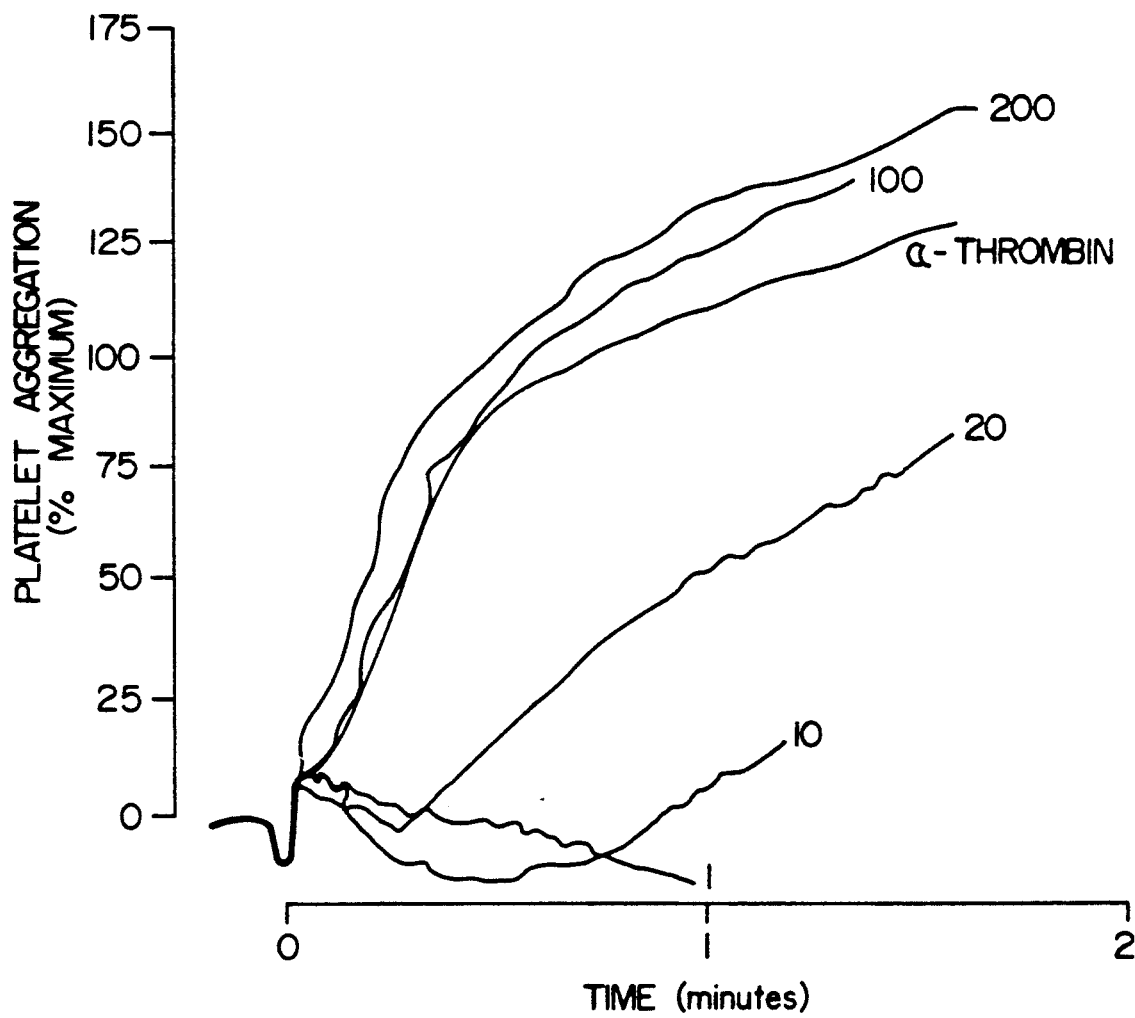
FIGS. 3A to C show platelet response to agonist peptide.

Platelet aggregation in response to 1, 10, 20, 100 or 200 μM peptide SFLLRNPNDKYEPF or to 20 nM thrombin was measured in a lumiaggregometer, and the results are shown in FIG. 3A.

Figure 3B:
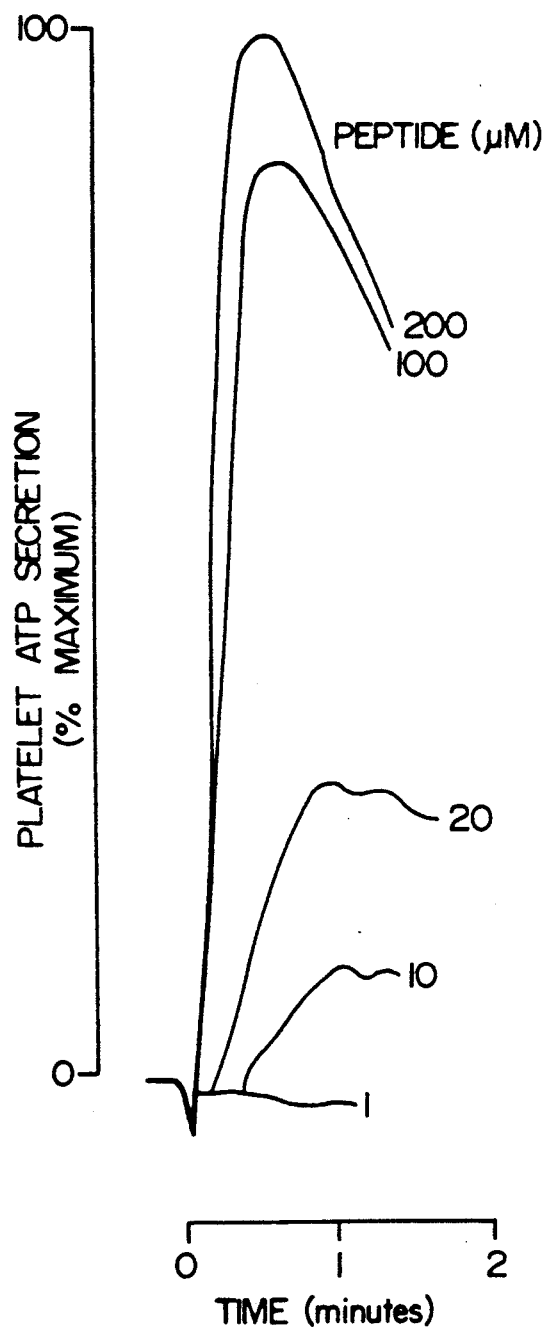

Platelet ATP secretion in response to the indicated final concentrations of "new amino-terminal" peptide was also followed by lumiaggregometry, and the results are shown in FIG. 3B.

Figure 3C:
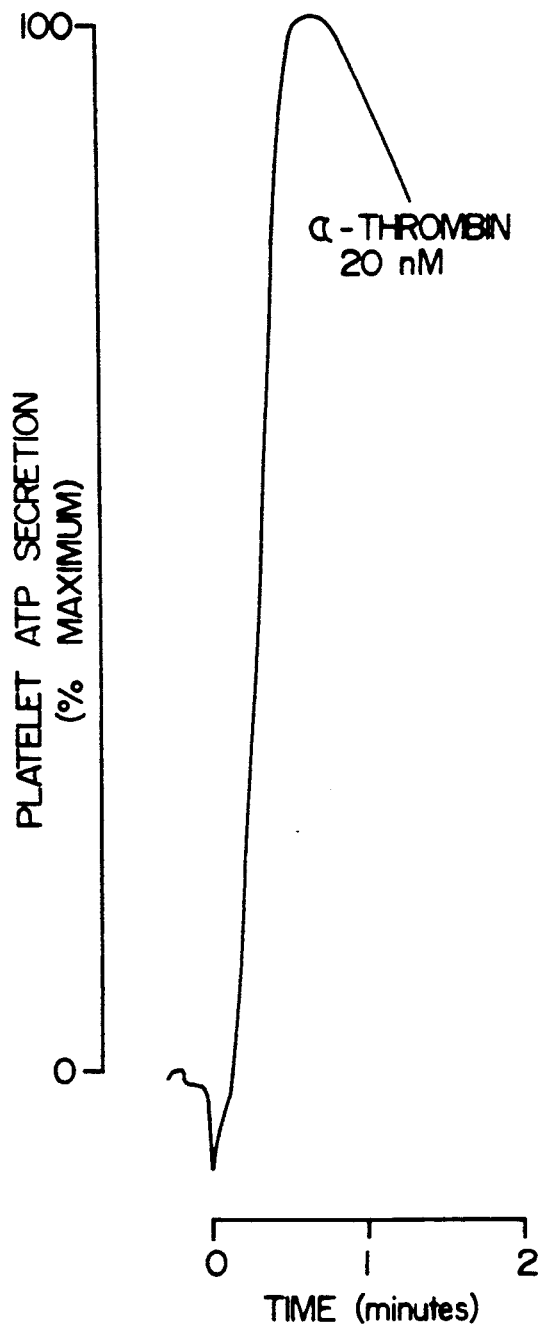

The data shown in FIGS. 3A to C are raw tracings representative of aggregation or secretion responses obtained in triplicate for each agonist concentration, and are representative of results obtained in more than five separate experiments. 100% aggregation is arbitrarily defined as that occurring in response to a saturating concentration of thrombin at one minute. 100% secretion is arbitrarily defined as the maximal response occurring in response to a saturating concentration of thrombin. The "new amino terminal" peptide is comparably active to 20 μM thrombin at concentrations of 100 μM in both assays as shown in the figure. The control peptides FSLLRNPNDKYEPF and LLRNPNDKYEPF were both without activity at concentrations as high as 200 μM (not shown).

In an additional determination, the mitogenic effects of the agonist peptide were demonstrated using CCL-39 cells. The fibroblast cell line CCL-39 was made quiescent in serum-free medium and then treated for 48 hours with the candidate agonist in the presence of tritiated thymidine. The incorporation of label into DNA was then determined as TCA-insoluble activity, shown as cpm in FIG. 4 using standard techniques. The data shown in the figure represent the mean of six replicate determinations plus or minus 95% confidence.

The agonists shown in the figure were:
None (serum-free);
10% fetal bovine serum (10% FCS);
100 nM α-thrombin (a-T);
1, 10 or 100 μM agonist peptide of the sequence SFLLRNPNDKYEPF (NTP);
1, 10 or 100 μM agonist peptide of the sequence SFLLRNPNDKYEPF (NTP);
100 μM ¢scrambled" agonist peptide, which is the foregoing with the N-terminus scrambled to FS (FSLL).

Figure 4:
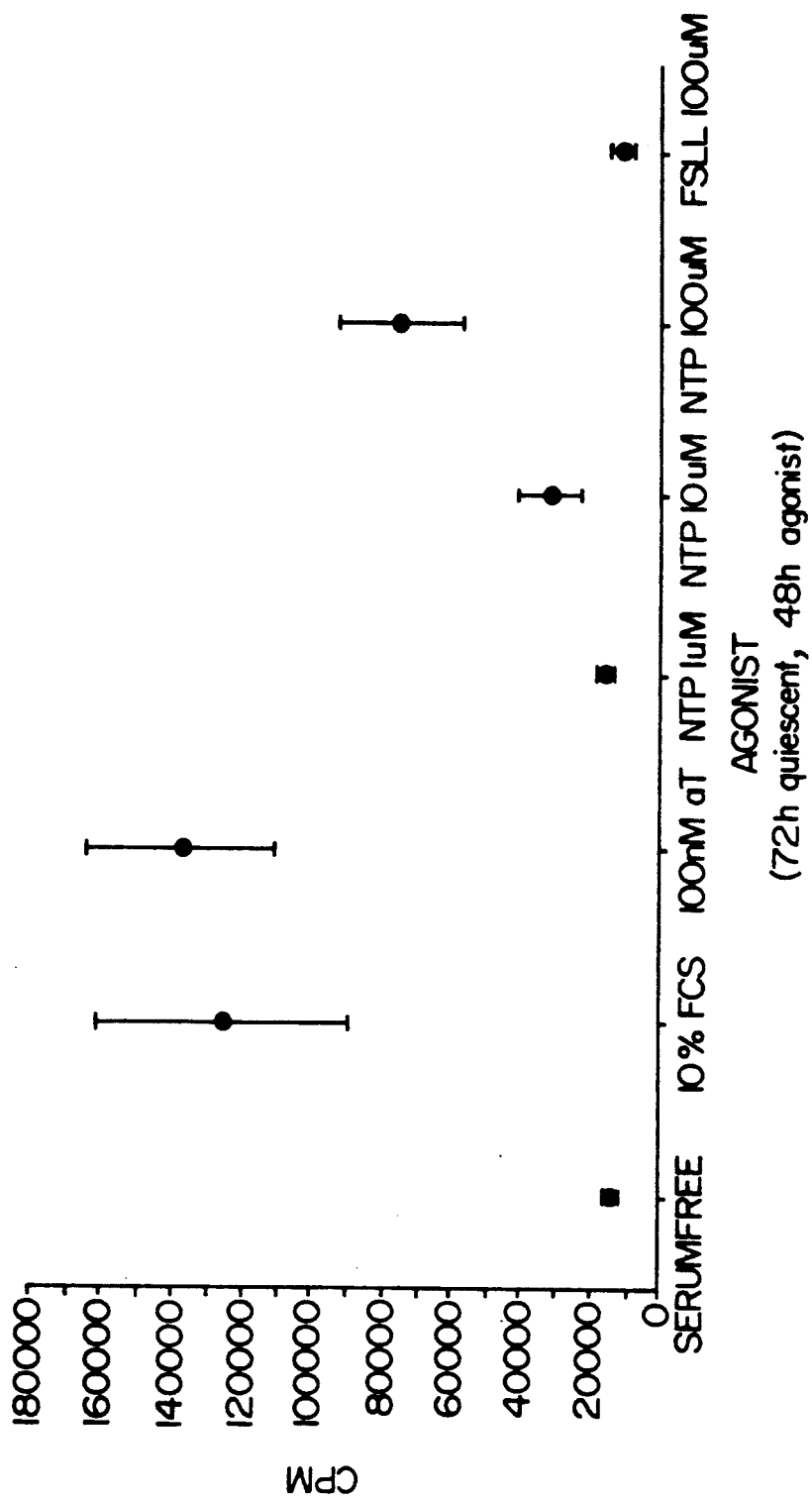
FIG. 4 shows the mitogenic effect of an agonist peptide of the invention on fibroblasts.

As shown in FIG. 4, the NTP at 100 μM gives significant stimulation of growth. Merely switching the positions of the first two residues of the agonist caused loss of activity. Thus, the agonist peptide not only simulates platelet aggregation, but also is useful in stimulating fibroblast proliferation, which is useful in wound-healing applications.

EXAMPLE 4

Inhibition of Thrombin-Induced Platelet Activation by Antagonist Peptides

Two antagonist peptides of the invention, LDPRPFLLRNPNDKYEPFWEDEEKNES (LDPRP peptide) and F$^t$PRPFLLRNPNDKYEPF-WEDEEKNES (F$^t$PRP peptide), were tested for their ability to inhibit thrombin-induced platelet activation. Thrombin was incubated with the candidate inhibitory peptide for 5 minutes, then the mixture was added to washed platelets and platelet activation was followed as platelet ATP secretion by lumiaggregometry. The results are shown in FIGS. 5 and 6.

Figure 5:
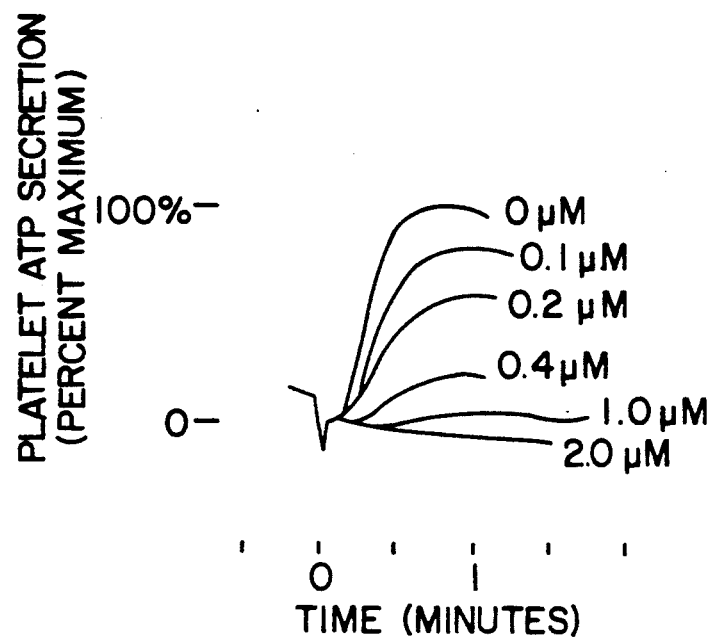
FIG. 5 shows the effect of a receptor-based antagonist peptide, LDPRP peptide, on thrombin-induced platelet activation.

In FIG. 5, the results for LDPRP peptide are shown as lumiaggregometer curves. In FIG. 5, the final concentration of thrombin was 1 nM for all curves; the concentration of the LDPRP peptide in μM is shown at the right of the curves. One hundred percent ATP secretion is defined as the maximum platelet secretion occurring in response to 1 nM thrombin in the absence of inhibitor. The IC$_{50}$ for the LDPRP peptide is approximately 200 nM. This peptide also blocked thrombin-induced platelet aggregation.

Figure 6:
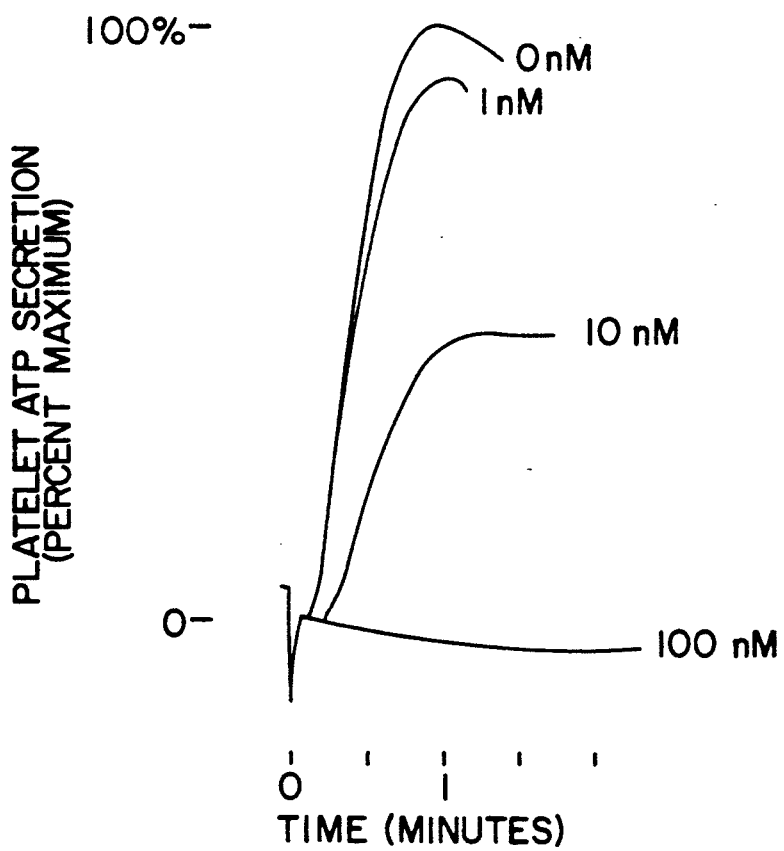
FIG. 6 shows the effect of an additional antagonist peptide, F PRP peptide, on thrombin-induced platelet activation.

FIG. 6 shows corresponding results with the F$^t$PRP peptide. The assay was conducted as for FIG. 5, the but the final concentration of thrombin was 2 nM for all curves. The concentration of the F$^t$PRP is shown in nM to the right of each curve. The IC$_{50}$ for F$^t$PRP peptide is about 10 nM. This peptide also blocked platelet aggregation, and is over 20-fold more potent than the LDPRP peptide.

EXAMPLE 5

Generation of Active-site Thrombin Mutants

Oligonucleotide-directed mutagenesis (Kunkel, T. A., et al., Meth Enzymol (1987) 154:367-383) was used to generate the active-site residue substitutions S205A and D99N/S205A in a native prothrombin cDNA cloned into a Bluescript SK-plasmid vector system (Stratagene, La Jolla, Calif.). After confirmation by DNA sequencing, DNA coding for prothrombin with the desired mutation(s) in the thrombin active site as well as native prothrombin cDNA were subcloned into a pBJ1 expression vector (derived from pcDL-SRα296) (Takabe, Y., et al., *Mol Cell Biol* (1988) 8:466–472) and cotransfected into dihydrofolate reductase (DHFR)-minus CHO cells by lipofection (Felgner, P., et al., *Proc Natl Acad Sci* U.S.A. (1987) 84:7413–7417) with a DHFR selection marker in pSV2D (Sabramani, S., et al., *Mol Cell Biol* (1981) 2:854–864). Stable transfectants were isolated and gene amplification was accomplished in 80 nM methotrexate.

Recombinant prothrombin production was determined by ELISA and Western blots and the highest yielding clones were grown to confluence in a 24,000 cm$^2$ surface cell "factory" (Nunc, Inter Med, Naperville, Ill.) in MEM α-nucleoside-deficient medium with 80 nM methotrexate, 100 units/ml penicillin, 100 μg/ml streptomycin, 25 mM Hepes buffer, 5 μg/ml vitamin K, 0.2 mg/ml proline, and 10% dialyzed bovine calf serum. Upon reaching full confluence, all medium was removed, all growing surfaces washed six times with phosphate-buffered saline to remove contaminating bovine prothrombin and thrombin, and cells were grown in MEM α-nucleoside-deficient medium containing 100 units/ml penicillin, 100 μg/ml streptomycin, 25 mM Hepes buffer, 5 μg/ml vitamin K, 0.2 mg/ml proline, 1 μg/ml insulin and 5 μg/ml transferrin for 36–48 hours.

Conditioned medium was cleared of cellular debris by centrifugation and filtration, diluted I:1 with water, made to 10 mM Tris-HCl, pH 7.4, and 20 mM citrate (final concentration) and stirred overnight at 4° C. with 1% (v/v) S-Sepharose. S-Sepharose beads were removed by centrifugation and the conditioned medium was refiltered and stirred overnight at 4° C. with 1% (v/v) Q-Sepharose. Q-Sepharose was then collected in a 10 ml column and eluted in 1 ml fractions with 600 mM NaCl, 10 mM Tris-HCl, pH 7.4, 0.5% PEG 6000 and positive fractions containing recombinant prothrombin identified by Western blot using anti-human thrombin antiserum.

Positive fractions were pooled, diluted to an estimated concentration of 100 μg/ml S205A mutant prothrombin in 150 mM NaCl, 10 mM Tris-HCl, pH 7.4, 0.5% PEG 6000 and treated for 1 hr with prothrombinase complex as previously described (Krishaswamy, S., et al., *J Biol Chem* (1987) 262:3291–3299). pH was then changed to 7.0 with 1M HCl and the S205A or D99N/S205A mutant thrombin-containing solution was treated with an approximately 1,000-fold molar excess of (p-amidinophenyl)-methanesulfonyl fluoride (APMSF) to inhibit Factor Xa and any bovine thrombin that might contaminate the preparation. APMSF is a serine-dependent irreversible thrombin antagonist that rapidly inactivates native thrombin at pH 7.0 but has a half-life of only $10^{-3}$ sec at pH 8.0. For this reason, the pH of the APMSF-treated mutant thrombin preparation was then changed to 8.0 for 15 min to eliminate all APMSF.

The mutant thrombin-containing solution was then changed to pH 6.0 by addition of 1N HCl and stirred overnight at 4° C. with 1% (v/v) S-Sepharose. The S-Sepharose was collected in a 10 ml column, washed with 50 mM NaCl, 10 mM MES, pH 6.0 and subsequently eluted with 600 mM NaCl, 10 mM MES, pH 6.0, 0.5% PEG 6000 in ml fractions. Positive fractions were identified by Western blot with anti-human thrombin antiserum and the concentration and purity of recombinant S205A or D99N/S205A thrombin preparations were determined by Coomassie and silver-stained SDS-PAGE gels. The mutant thrombin preparations used in these studies appeared homogeneous on silver-stained SDS-PAGE gels.

EXAMPLE 6

Fibrinogen Clotting Assay

Fibrinogen clotting activity was measured by a standard Fibro System ® coagulation timer (Fisher Scientific, Springfield, N.J.) as the time required for varying thrombin concentrations to generate a fibrin clot. All fibrinogen clotting reactions were performed in a total volume of 300 μl, in 150 mM NaCl, 20 mM Tris, pH 7.4, 10 mM CaCl$_2$, 0.5% PEG 6000 at 37° C. with a final fibrinogen concentration of 3.3 mg/ml. Both standard WT and recombinant WT showed identical curves—e.g., about 10 second clotting times at 5 nM. Neither S205A nor D99N/S205A were able to induce clotting.

EXAMPLE 7

Platelet ATP Secretion and Aggregation Studies

Washed platelets were prepared as described above and suspended in modified Tyrode' buffer, pH 7.4 with 2 mM magnesium and 1 mM calcium at a concentration of $10^8$ platelets/ml. All platelet studies were performed in a total volume of 500 μl with 20 μl Chromolume ® reagent (Chronolog Corporation, Havertown, Pa.). Platelet ATP secretion and aggregation were quantitated independently by measuring changes in luminescence and light transmittance, respectively, in a Chronolog dual-channel lumiaggregometer (Chronolog Corporation, Havertown, Pa.). Platelets were stirred at 300 rpm to ensure rapid and uniform distribution of agonist.

Figure 7:
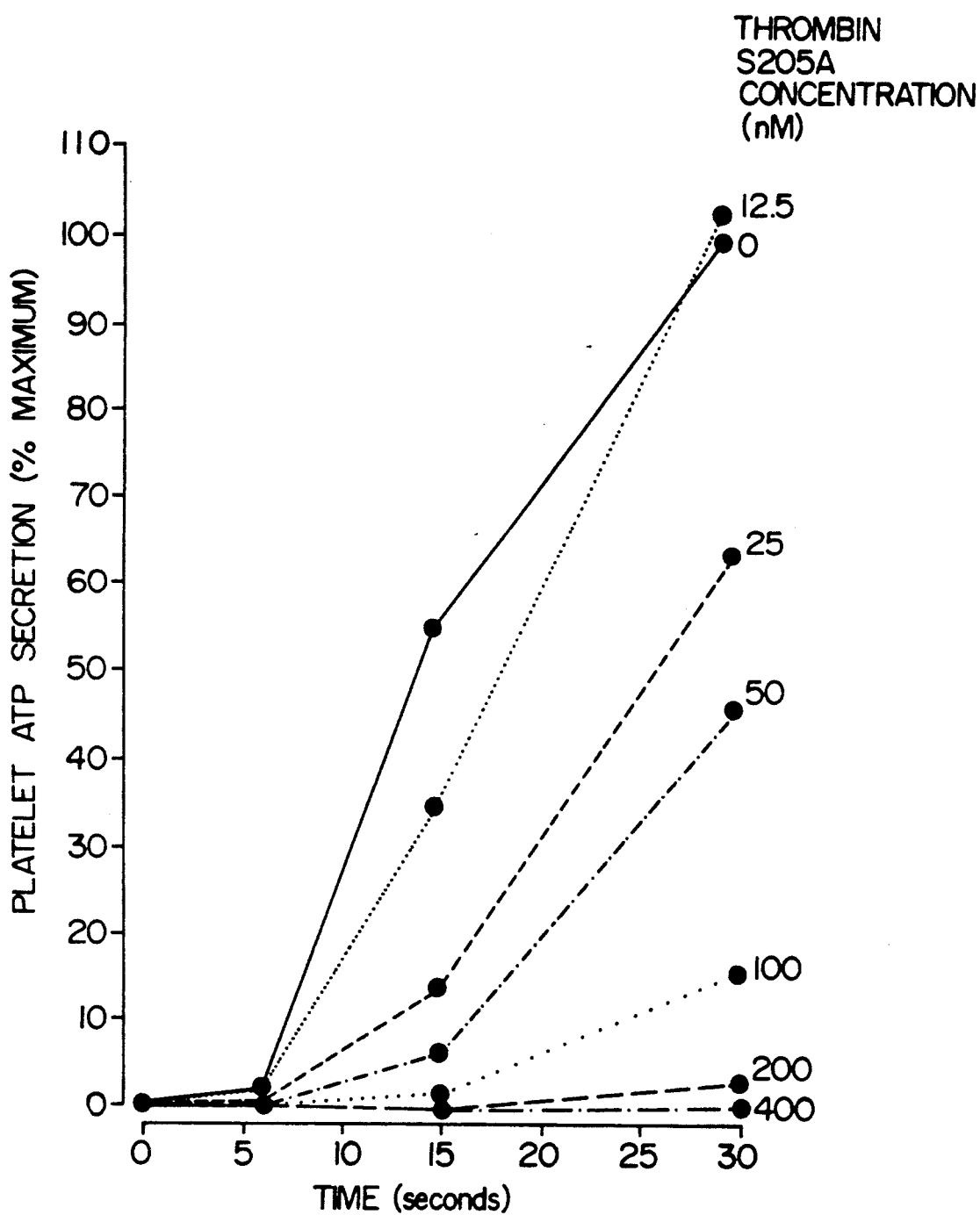
FIG. 7 shows the effect of mutant thrombin on platelet ATP secretion stimulated by thrombin.

500 μl of platelets were incubated for 15 minutes at 37° C. with 18 μl of diluted S205A stock in 600 mM NaCl, 10 mM MES, pH 6.0, 0.5% PEG 6000 buffer to give the desired final concentrations, or 18 μl of buffer alone and then challenged with native thrombin (1 mM final concentration). Platelet ATP secretion and aggregation were followed for 30 seconds after thrombin addition. Platelet ATP secretion data are expressed as a percentage of maximum, defined as the luminescence signal obtained 30 seconds after addition of 1 mM native thrombin to buffer-pretreated platelets. The results are shown in FIG. 7. Each point represents the mean of three replicate determinations, and are representative of three replicate experiments. As shown, increasing concentrations of S205A thrombin cause increasing inhibition of thrombin-induced platelet secretion. Similar results were obtained using the D99N/S205A mutant thrombin.

Figure 8:
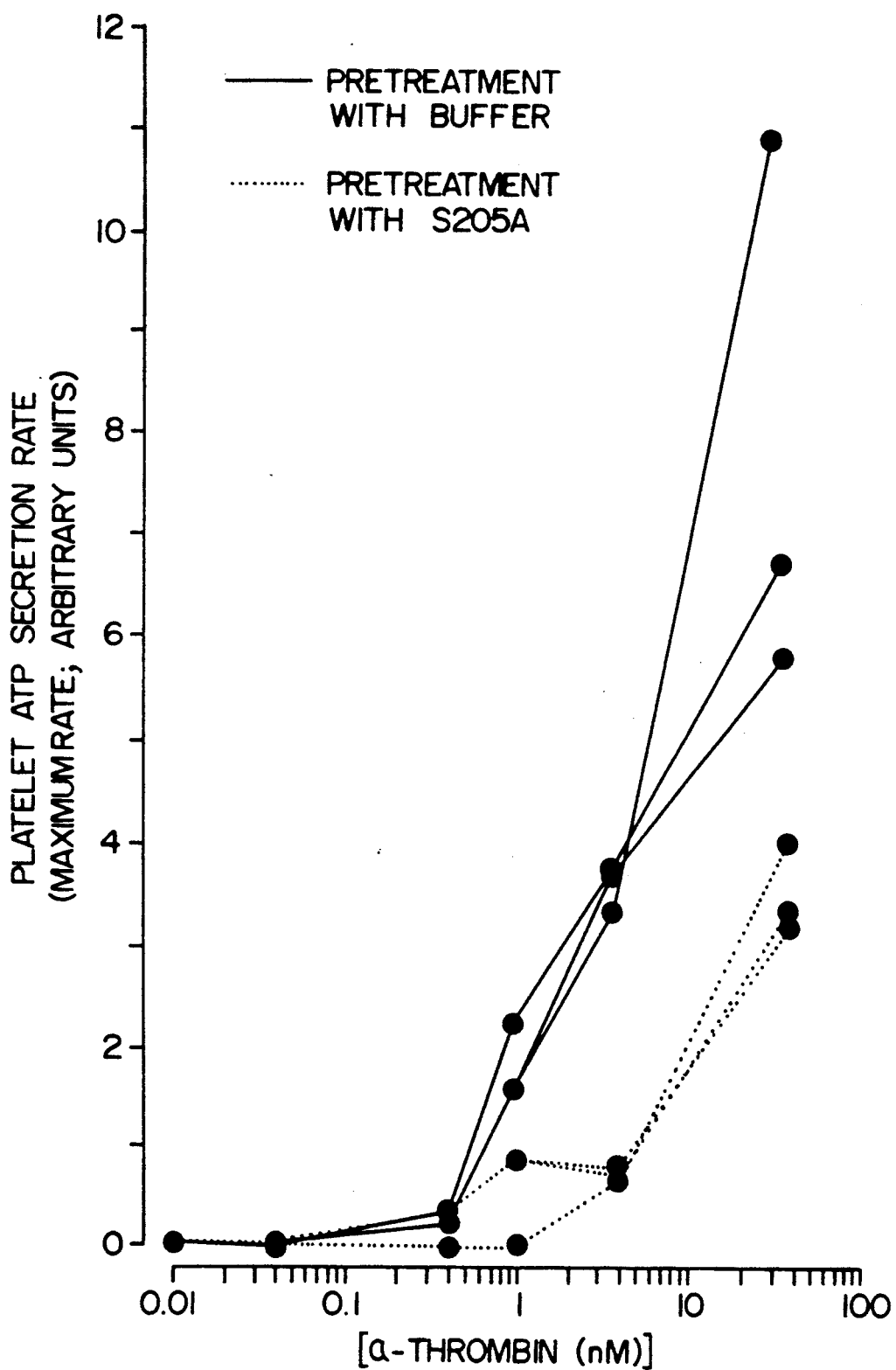
FIG. 8 shows the increase in thrombin needed to overcome inhibition of platelet ATP secretion by mutant thrombin.

In an additional determination it was shown (FIG. 8) that 400 nM S205A thrombin right-shifts the dose response of platelets to native thrombin by approximately 1 log. In this determination, 18 μl of S205A in 600 mM NaCl, 10 mM MES, pH 6.0, 0.5% PEG 6000 buffer to give a final S205A concentration of 400 nM) or an equal volume of buffer alone (solid lines) were incubated with 500 μl of platelets for 15 minutes at 37° C. Platelets were then stimulated with the indicated final concentrations of o-thrombin; platelet ATP secretion and aggregation were followed for 30 seconds after thrombin addition. The date shown reflect the maximum initial rate of platelet ATP secretion, specifically, the maximum rate of platelet ATP secretion occurring within 30 seconds of agonist addition and before any aggregation was detected. Thus, the platelet ATP secretion rates reported represent only agonist-induced and not aggregation-induced responses. Curves from three replicate experiments are shown in FIG. 5. One arbitrary unit corresponds to 33 pmoles of ATP released per second based on calibration with ATP standards.

An additional experiment shows S205A thrombin inhibits the extent of native thrombin-induced platelet secretion. Platelets were preincubated with various concentrations of S205A, then stimulated with native thrombin (1 nM final concentration). To prevent aggregation-induced secretion, platelets in these experiments were suspended to a final concentration of $2 \times 10^7$ platelets/ml and were not stirred after the addition of native thrombin. Under these conditions, platelets did not aggregate but did secrete ATP in response to thrombin. Platelet secretion rate is expressed in arbitrary units as defined above. FIG. 6 shows tracings of platelet secretion curves, and are representative of the results obtained in three replicate experiments. The decrease in luminescence seen in the control curve (0 nM S205A thrombin) is characteristic of the assay and may represent end-product inhibition of luciferase.

Figure 9:
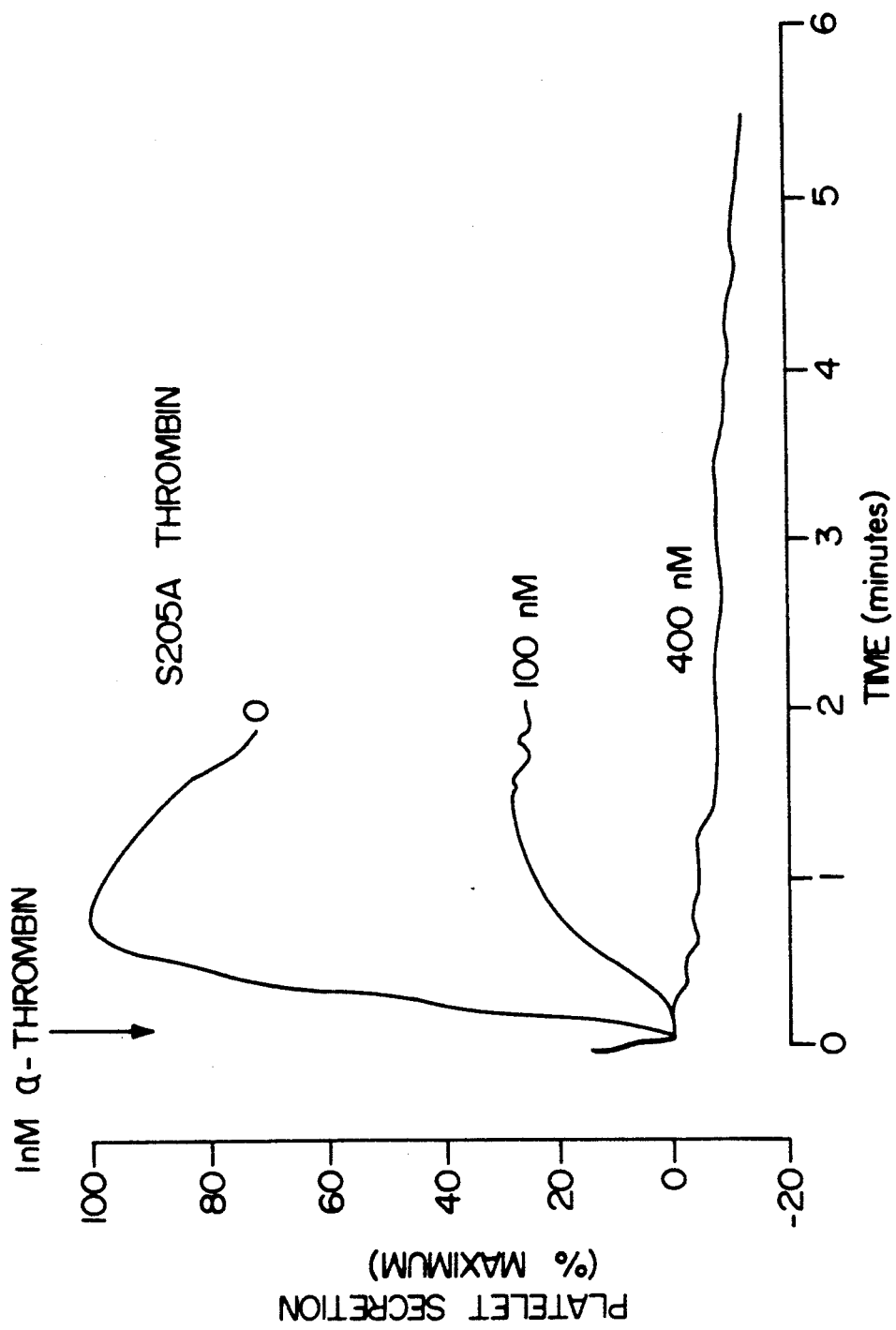
FIG. 9 shows the effect of thrombin on platelet ATP secretion by varying concentrations of thrombin mutant.

However, S205A thrombin does not inhibit collagen-induced platelet secretion. Platelets were preincubated with mutant thrombin (400 nM final concentration) or an equal volume of saline buffer and than challenged with either native thrombin (1 nM final concentration) or 20 μg/ml native equine collagen fibril type I (Chronolog Corporation, Havertown, Pa.). Maximal platelet ATP secretion rate is expressed in arbitrary units corresponding to those in FIG. 9 in Table 2. Maximal platelet ATP secretion rates reflect the mean (+/− standard deviation) of three replicate determinations and are representative of three replicate experiments.

TABLE 2

| Antagonist | Agonist | ATP Secretion |
|---|---|---|
| Buffer | Thrombin | 1.4 |
| S205A | Thrombin | 0 |
| Buffer | Collagen | 0.4 |
| Thrombin | Collagen | 0.4 |

---

What is claimed is:

1. A purified or isolated peptide capable of activating thrombin receptor which is selected from the group consisting of SFLLRNPNDKYEPF; SFLLRNPNDKYEP; SFLLRNPNDKYE; SFLLRNPNDKY; SFLLRNPNDK; SFLLRNPND; SFLLRNPN; SFLLRNP; SFLLRN; SFLLR; SFLL; and SFL, and the amidated forms thereof.

2. A pharmaceutical composition useful for wound healing which comprises an effective amount of the peptide of claim 1 in admixture with at least one pharmaceutically acceptable excipient.

3. A method to effect wound healing which comprises administering to said wound an effective amount or the peptide of claim 1 or a pharmaceutical composition thereof.

4. The peptide of claim 1 which is SFLLRNPNDKYEPF or the amidated form thereof.

5. The peptide of claim 1 which is SFLLRNPNDKYEP or the amidated form thereof.

6. The peptide of claim 1 which is SFLLRNPNDKYE or the amidated form thereof.

7. The peptide of claim 1 which is SFLLRNPNDKY or the amidated form thereof.

8. The peptide of claim 1 which is SFLLRNPNDK or the amidated form thereof.

9. The peptide of claim 1 which is SFLLRNPND or the amidated form thereof.

10. The peptide of claim 1 which is SFLLRNPN or the amidated form thereof.

11. The peptide of claim 1 which is SFLLRNP or the amidated form thereof.

12. The peptide of claim 1 which is SFLLRN or the amidated form thereof.

13. The peptide of claim 1 which is SFLLR or the amidated form thereof.

14. The peptide of claim 1 which is SFLL or the amidated form thereof.

15. A pharmaceutical composition useful for wound healing which comprises an effective amount of the peptide of claim 14 in admixture with at least one pharmaceutically acceptable excipient.

16. A method to effect wound healing which comprises administering to said wound an effective amount of the peptide of claim 14 or a pharmaceutical composition thereof.

* * * * *